United States Patent [19]

Miyata et al.

[11] Patent Number: 5,436,141
[45] Date of Patent: Jul. 25, 1995

[54] METHOD FOR SYNTHESIZING STABLE SINGLE-STRANDED CDNA IN EUKARYOTES BY MEANS OF A BACTERIAL RETRON AND PRODUCTS

[75] Inventors: Shohei Miyata, Misato, Japan; Atsushi Ohshima, Highland Park, N.J.; Sumiko Inouye; Masayori Inouye, both of Bridgewater, N.J.

[73] Assignee: University of Medicine and Dentistry of New Jersey, Newark, N.J.

[21] Appl. No.: 753,110

[22] Filed: Aug. 30, 1991

Related U.S. Application Data

[63] Continuation-in-part of Ser. No. 315,427, Feb. 24, 1989, Pat. No. 5,079,151, and a continuation-in-part of Ser. No. 315,316, Feb. 24, 1989, Pat. No. 5,320,958, and a continuation-in-part of Ser. No. 315,432, Feb. 24, 1989, abandoned, and a continuation-in-part of Ser. No. 517,946, May 2, 1990, and a continuation-in-part of Ser. No. 518,749, May 2, 1990.

[51] Int. Cl.⁶ .......................... C12N 1/19; C12N 5/10; C12N 15/81; C12P 19/34
[52] U.S. Cl. ................... 435/91.1; 435/240.2; 435/254.2; 435/254.21; 435/320.1; 536/25.2
[58] Field of Search ............ 435/91.1, 69.1, 320.1, 435/252.33, 194, 254.21, 256, 240.2, 240.21, 240.4, 254.2; 536/27, 25.2

[56] References Cited

U.S. PATENT DOCUMENTS

5,079,151 1/1992 Lampson et al. ............... 435/91.51

FOREIGN PATENT DOCUMENTS

0132309 1/1985 European Pat. Off. ...... C12N 15/00

OTHER PUBLICATIONS

Dhundale et al., *J. Bact.*, vol. 170, 1988, pp. 5620–5624.
Lampson et al., *Science*, vol. 243, 1989, pp. 1033–1038.
Sambrook et al., *Molecular Cloning: A Laboratory Manual*, Cold Spring Harbor Laboratory Press, 1989, pp. 16.15–16.16.

*Primary Examiner*—Richard A. Schwartz
*Assistant Examiner*—James Ketter
*Attorney, Agent, or Firm*—Weiser & Associates

[57] ABSTRACT

A method for producing in vivo stable single-stranded DNAs in eucaryotic cells. The DNAs are multicopy single-stranded DNA (msDNA) structures constituted by a RNA and a DNA portion. The group of genes (retrons) producing said coupled RNA and DNA portions of the msDNAs and the gene encoding reverse transcriptase (RT). The transformed eucaryotes harboring these retrons. The new msDNAs which are encoded by the new retrons. The msDNAs can be used as vectors for antisense DNA and for amplification of inserted genes.

45 Claims, 17 Drawing Sheets

METHOD FOR SYNTHESIZING STABLE SINGLE-STRANDED CDNA IN EUKARYOTES BY MEANS OF A BACTERIAL RETRON AND PRODUCTS

RELATED PATENT APPLICATIONS

This is a continuation-in-part of patent applications Ser. No. 315,427 filed Feb. 24, 1989, now U.S. Pat. No. 5,079,151; 315,316 filed Feb. 24, 1989, now U.S. Pat. No. 5,320,958; 315,432 filed Feb. 24, 1989, now abandoned; 517,946 filed May 2, 1990 and 518,749 filed May 2, 1990.

FIELD OF THE INVENTION

The invention concerns the field of recombinant DNA. More particularly, the invention relates to an in vivo method of synthesis of stable single-stranded cDNA in eucaryotic cells by means of a bacterial retroelement called a retron. The invention also relates to new eucaryotic vectors carrying the necessary elements to produce the single-stranded DNA-RNA hybrid structures. Moreover, the invention relates to transfected eucaryotes, e.g., yeast, plant cells and mammalian cells. Uses are described for the new products.

BACKGROUND

Gram-negative bacteria such as *Myxococcus xanthus, Stigmatella aurantiaca* and *Escherichia coli* have been found to contain a retroelement called a retron. In TIBS, 16, 18–21 (1991a), the authors report on a peculiar type of satellite DNA, named multicopy single-stranded DNA (msDNA). These molecules are characterized by a structure which comprises a single-stranded DNA branching out of an internal guanosine residue of a single-stranded RNA molecule by a unique 2',5'-phosphodiester linkage. These molecules are thus single-stranded DNA-RNA hybrids. Reverse transcriptase is required for the synthesis of these msDNAs. In *Ann. Rev. Microbiol.*, 45, 163–186 (1991b), the authors present a comprehensive review on msDNAs. Also see msDNA in Bacteria, Lampson et al., *Progress in Nucleic Acid Research and Molecular Biology*, 60, 1–24.

The production of single-stranded cDNA by reverse transcriptase as a template is an obligatory step for RT-mediated transcription of retroelements. See *Retroelements*. See Weiner et al., *Ann. Rev. Biochem.*, 55, 631–661 (1986) for review. This includes integration of retroviruses into mammalian genomes, production of infectious retroviruses from pro-viruses integrated into genomes, retrotransposition of retroelements, and formation of pseudo genes in eucaryotic cells.

However, single-stranded cDNAs produced in vivo by RT have never been directly detected, probably because of their instability.

While the production of msDNAs in bacteria has been a most significant development, the in vivo production of single-stranded DNAs in eucaryotic cells, e.g., yeast or higher eucaryotic cells like plant and mammalian cells, is of even greater interest. Eucaryotes have well-known advantages over procaryotes for producing target molecules. There is an important need to produce stable single-stranded DNA in a sufficient yield for numerous practical uses in research and in industry. This invention has made an important contribution in that respect in producing single-stranded RNA-DNA structures which are detectible, stable and useful.

SUMMARY OF THE INVENTION

In accordance with the invention, a fundamental finding has been made. It has been discovered that single-stranded DNAs which are stable can be produced in vivo in eucaryotic cells.

Briefly described, the invention provides a method (or process) for producing in vivo stable, single-stranded DNAs in eucaryotic cells like yeasts or plant cells or mammalian cells. The method of the invention produces a single-stranded cDNA by means of a retroelement called a retron. The single-stranded DNA is produced as an integral part of a branched RNA-linked multicopy single-stranded DNA (msDNA) structure. These structures are stable, i.e., detectible after production and isolation in spite of the fact that they are constituted of RNA and DNA, both single-stranded. The method of the invention also provides such msDNAs which contain foreign DNA and RNA fragments in the DNA and RNA portions, respectively, of the RNA-DNA structure. Though different from the known bacterial msDNAs, these molecules are designated as msDNAs or "modified" msDNAs, because they have the characteristics and unique features of msDNAs as described herein.

The invention also provides retrons. Retrons are genetic elements which contain the coding region msr for the msRNA and msd for the msdDNA of the msDNA molecule, respectively, and the gene for reverse transcriptase (RT). The retrons which are new in accordance with the invention, have sequences which are different from known bacterial retrons in that the non-coding region has been shortened, specifically the region between the transcriptional initiation site of the selected promoter and the initiation codon of the RT gene.

The invention also provides retrons which are new by virtue of the fact that, unlike known bacterial retrons, the RT gene is positioned upstream of the msr-msd region, in reverse relationship of that in bacterial retrons. These new retrons produce greater yields of msDNAs.

The invention further provides new types of msDNAs which are new by virtue of having been produced by the novel retrons. These msDNAs contain a foreign DNA fragment in their DNA portion, for instance, a single-stranded fragment complementary to the mRNA of a particular target gene (antisense DNA) and thus, may be valuable tools to inhibit or change the expression of undesirable proteins. Similarly, msDNA can also contain a foreign RNA fragment.

Further novel embodiments of the invention are transformed eucaryotic hosts with retrons which have been identified from bacterial sources. Also new are eucaryotic hosts transfected with the new vectors discussed above.

Various uses for the new single-stranded RNA-DNA structures are described.

DEPOSIT OF GENETIC MATERIAL

Plasmid YEp521-M1 has been deposited with the American Type Culture Collection (ATCC) under Accession No. 74092.

Plasmid YEp521-M4 has been deposited with the ATCC under Accession No. 74093.

Plasmid YEp521-M5 has been deposited with the ATCC under Accession No. 74094. These plasmids were deposited on Aug. 28, 1991 with the American Type Culture Collection (ATCC), which is located at 12301 Parklawn Drive, Rockville, Md. 20852. All deposits were accepted by the ATCC on Aug. 28, 1991.

DETAILED DESCRIPTION OF THE FIGURES

Figure 1:
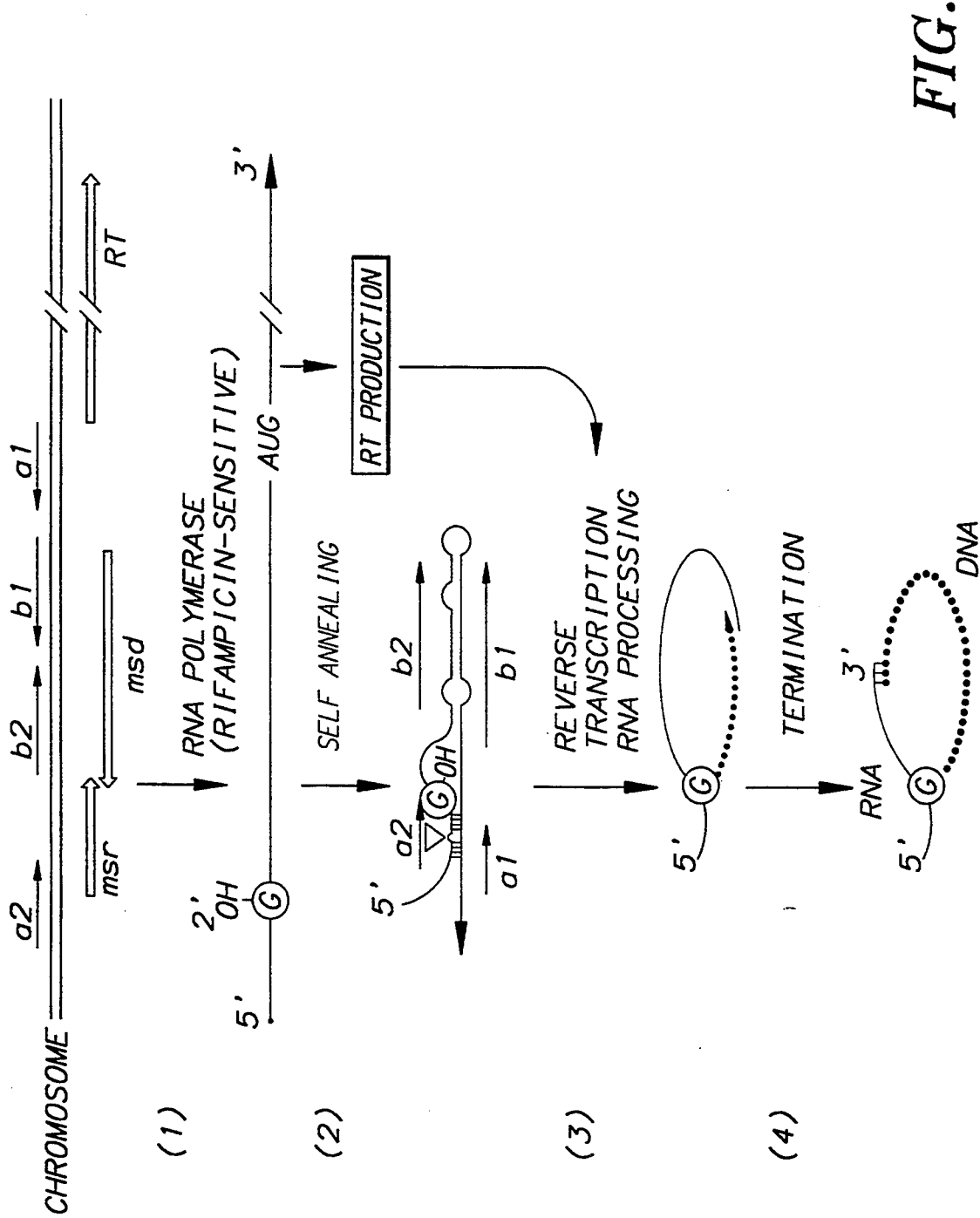
FIG. 1 illustrates the biosynthetic pathway of msDNA synthesis.
Figure 2A:
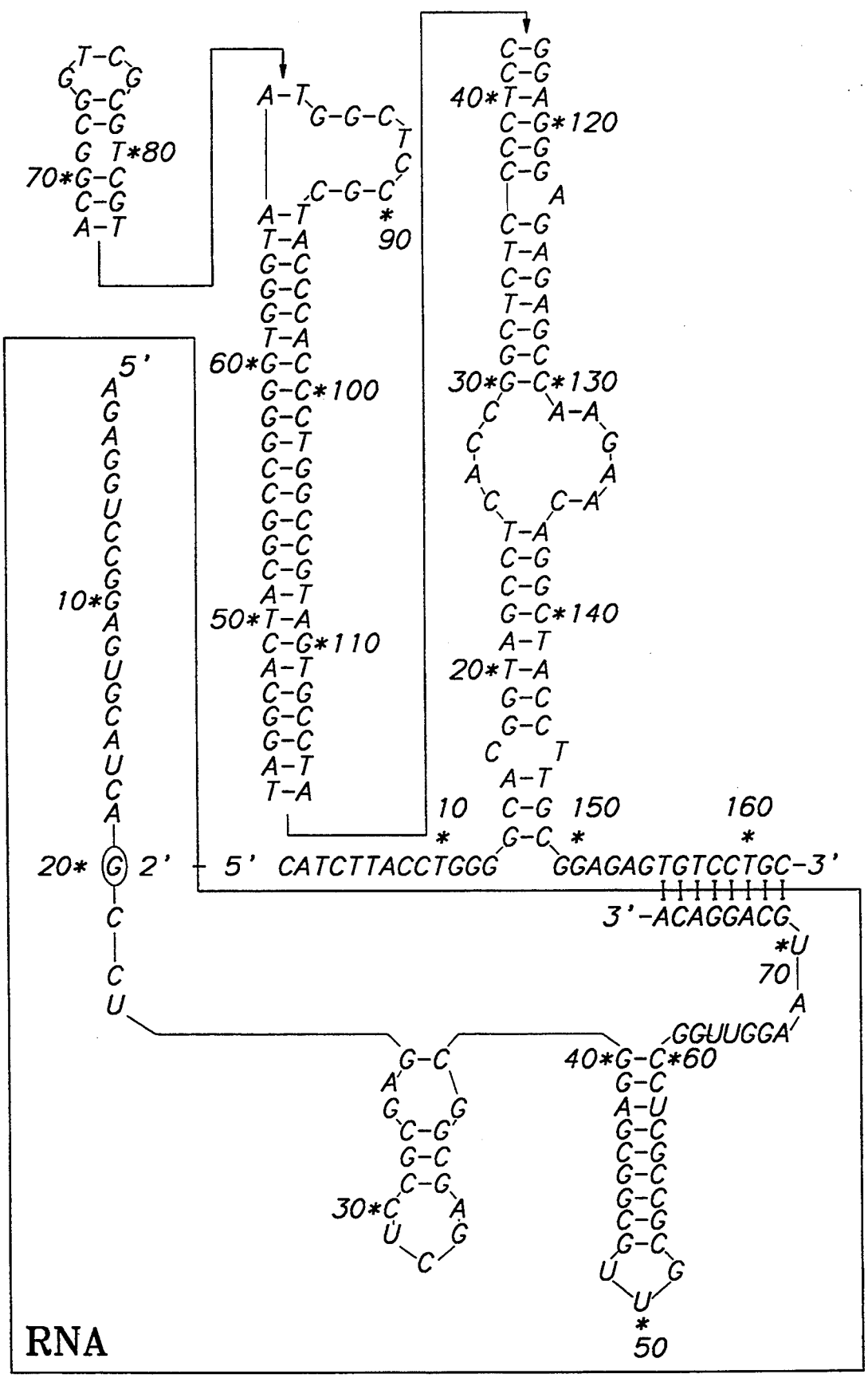
FIGS. 2(A–G) shows the structures of the typical bacterial msDNAs (SEQ. ID. NOS. 7–18).
FIG. 2H shows the structure of msDNA-Ye117 (SEQ.ID.NOS 13 AND 14).
Figure 2B:
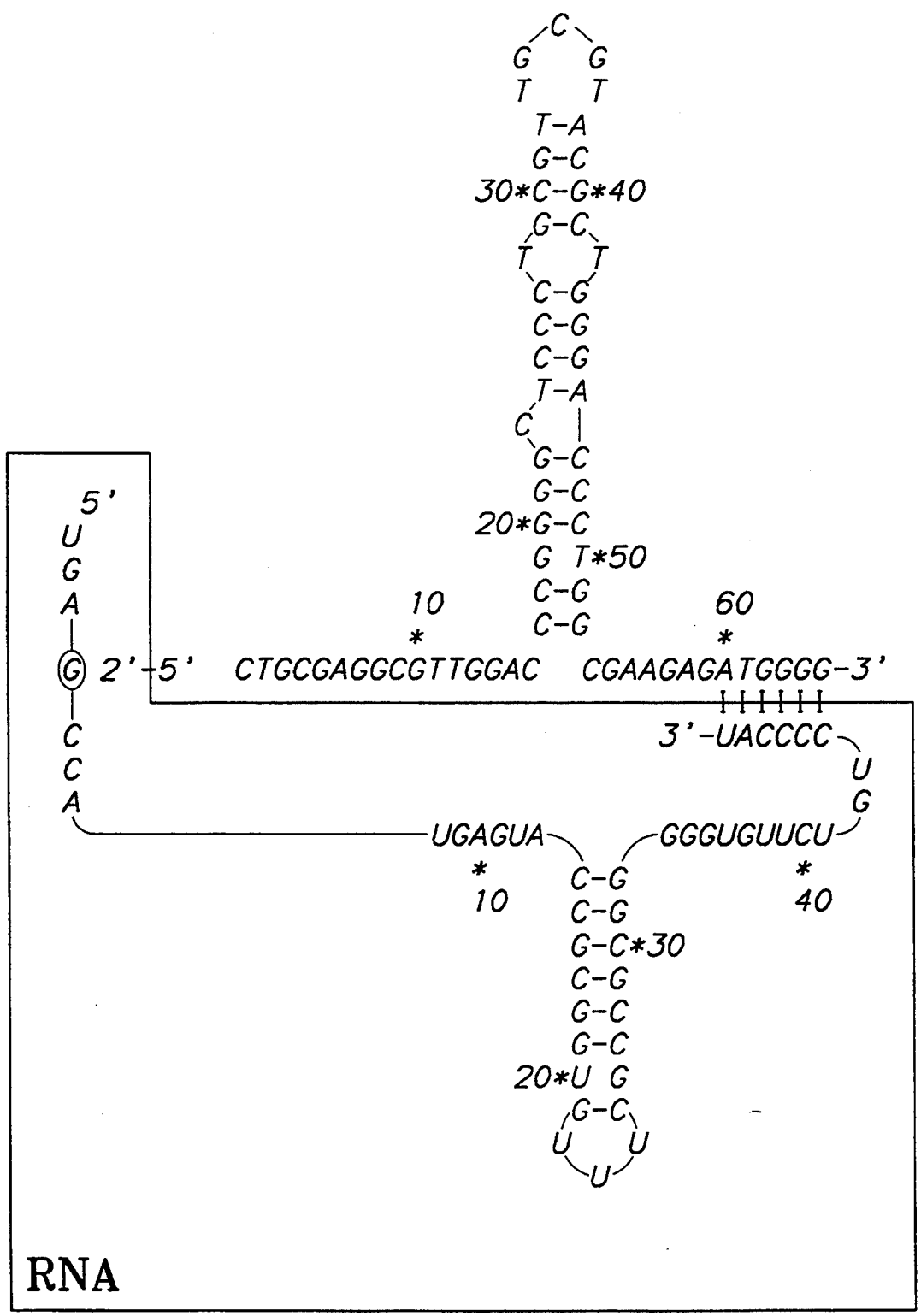
Figure 2C:
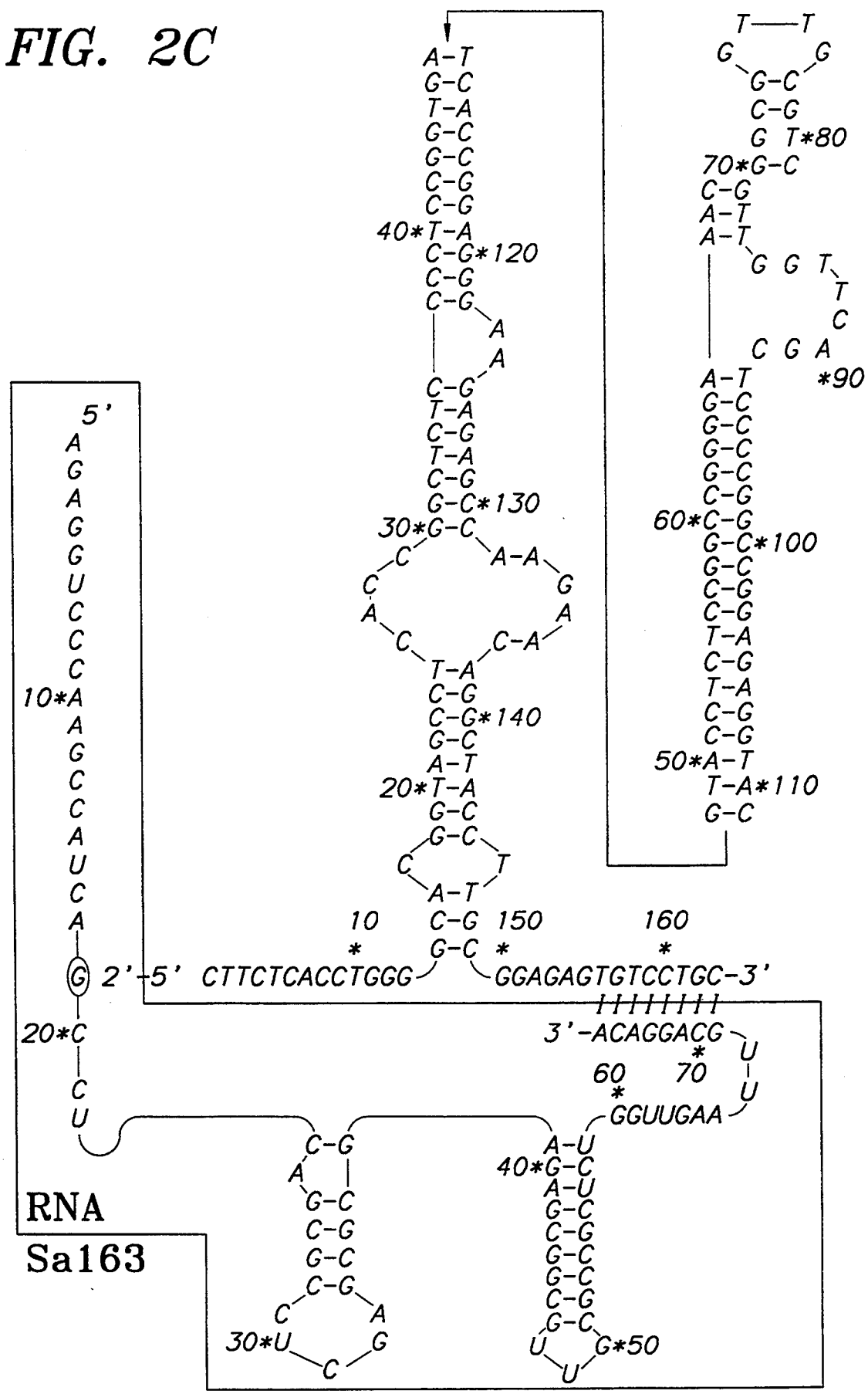
Figure 2D:
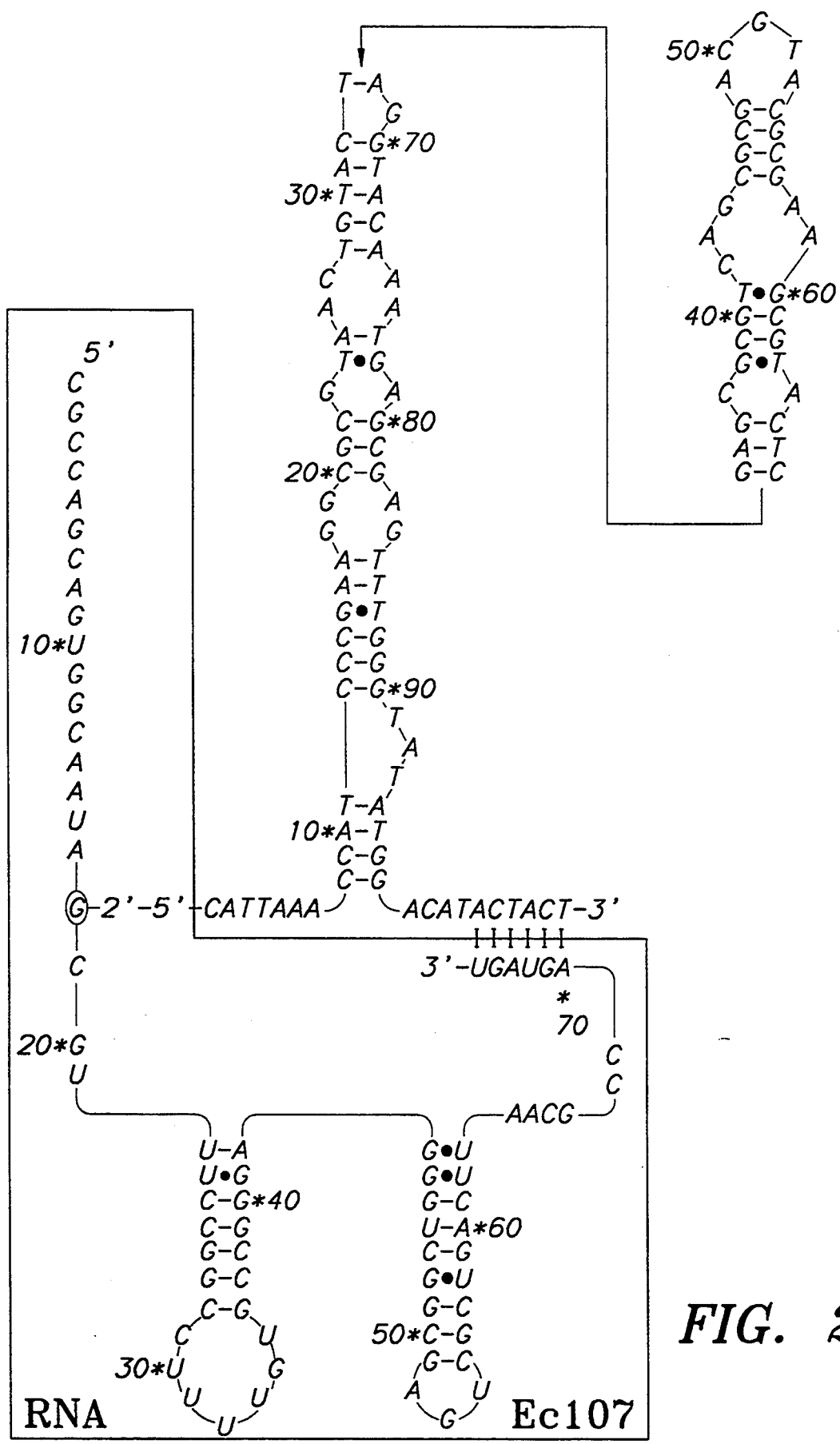
Figure 2E:
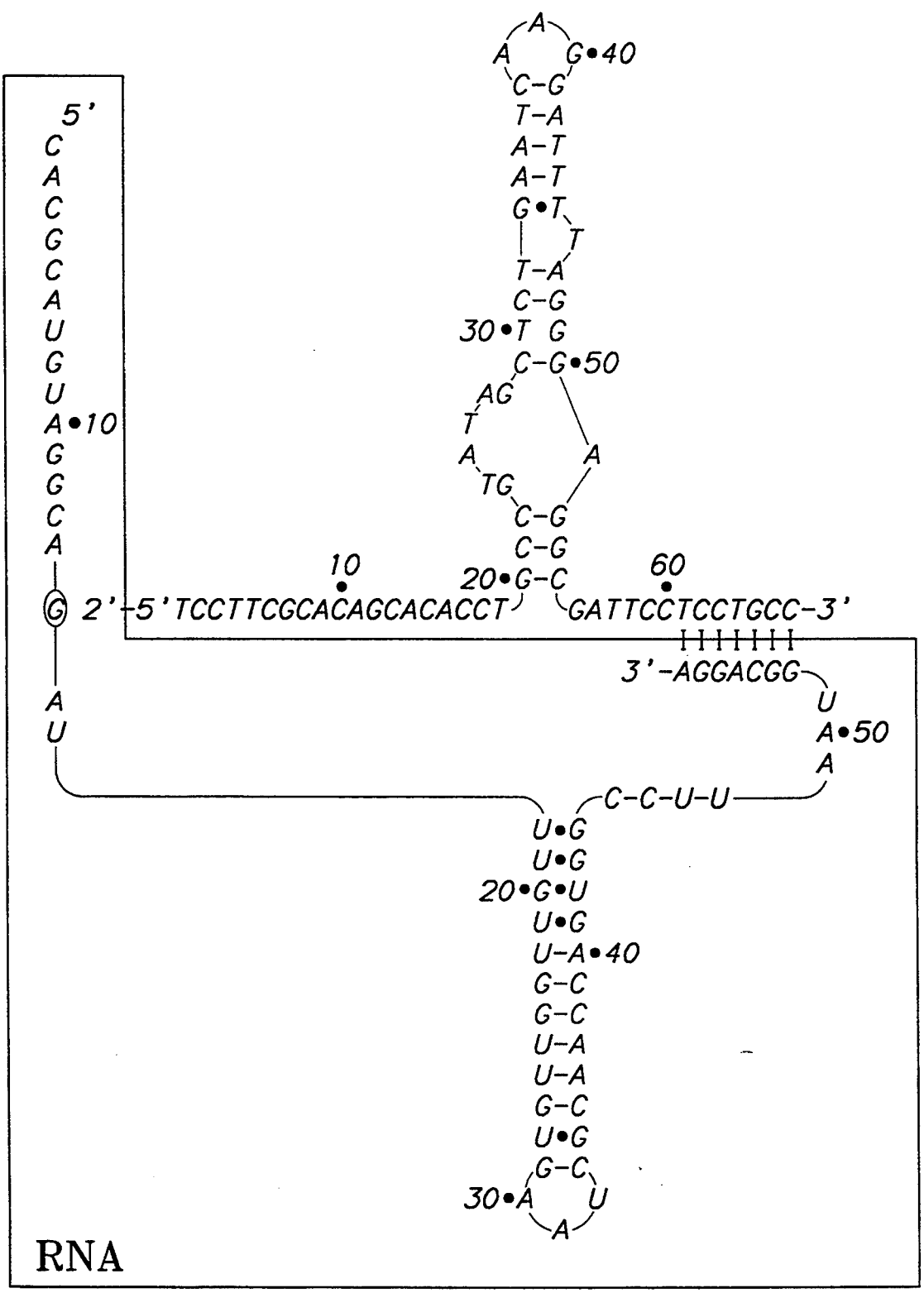
Figure 2F:
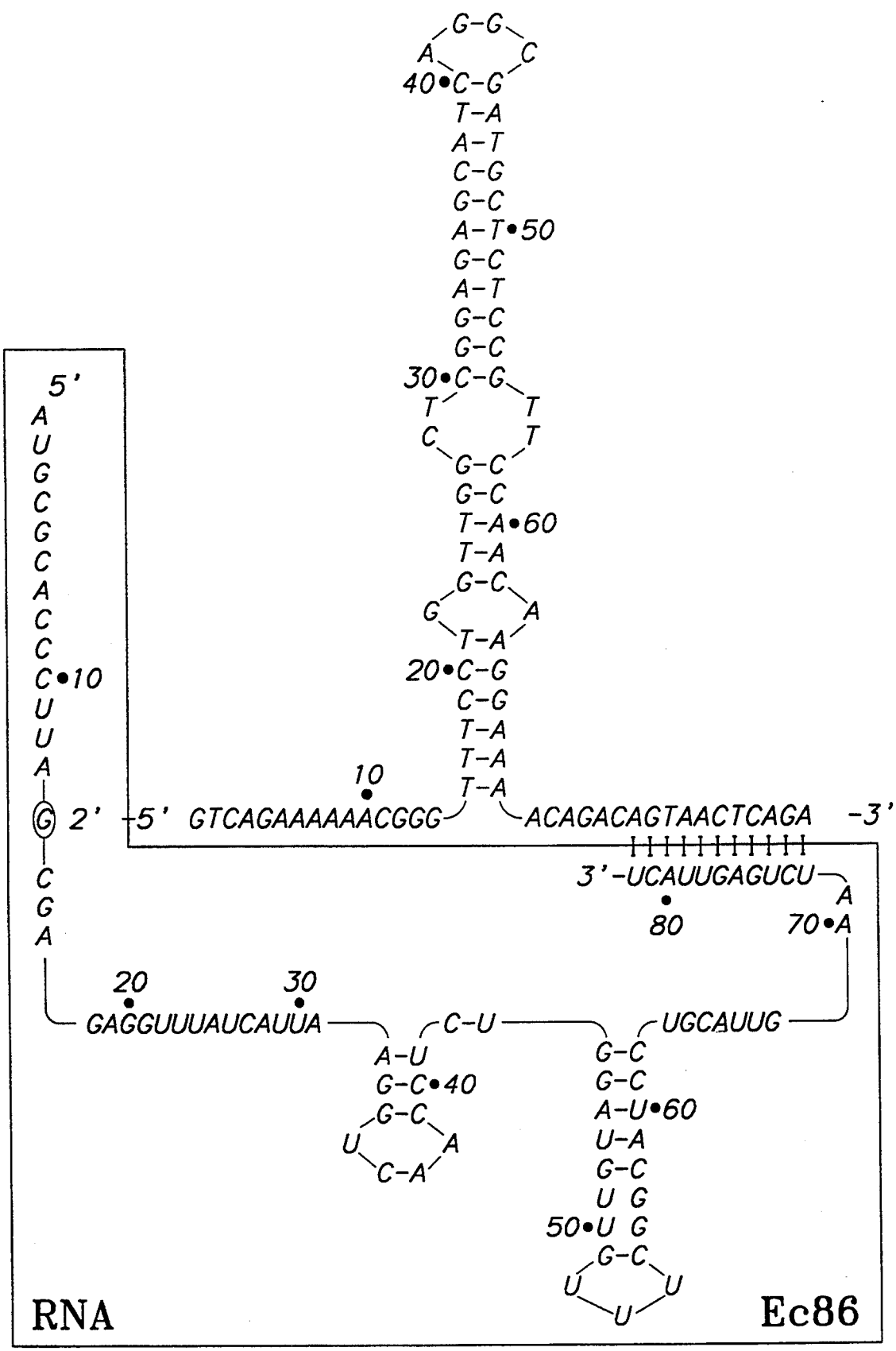
Figure 2G:
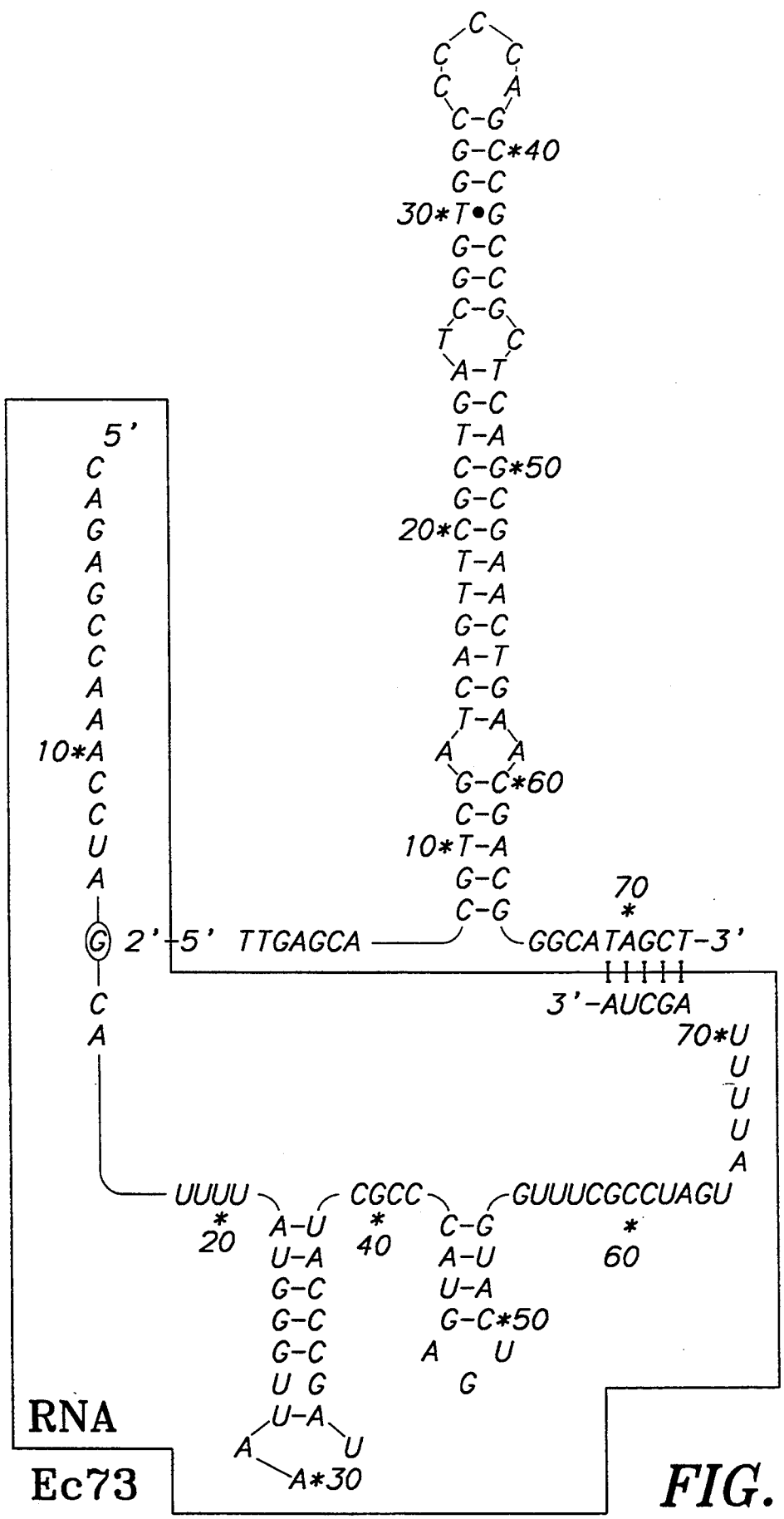
Figure 2H:
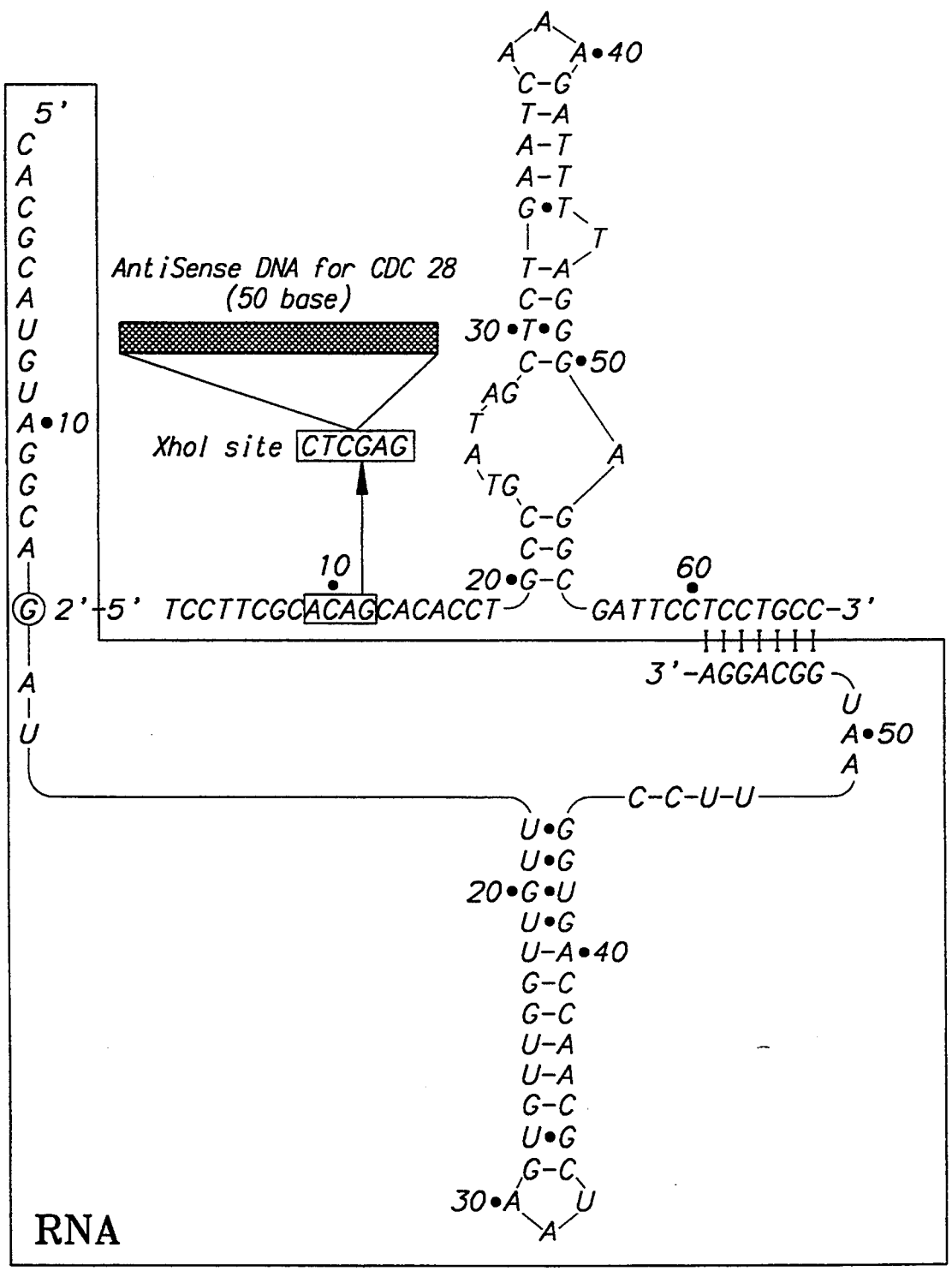

FIG. 1 Biosynthetic pathway of msDNA synthesis. The retron region consisting of the msr-msd region and the gene for reverse transcriptase (RT) is shown on the top of the Figure. Solid arrows indicate the locations of two sets of inverted repeats (a1 and a2, and b1 and b2). Open arrows indicate the genes for msdRNA (msr), msDNA (msd), and RT. The primary transcript is considered to encompass the upstream region of msr through the RT gene, which is shown by a thin line at step 1. The thick region in the RNA transcript corresponds to the final msdRNA. The branched G residue is circled, and the initiation codon for RT is also shown. On the folded RNA, a triangle indicates the 5' end processing site at the mismatching base. The dotted lines at steps 3 and 4 represent DNA strands.

FIG. 2 (A–G) Structures of hybrid DNA-RNA msDNA are shown as follows: Mx162 (Seq. ID Nos. 7 and 8), Mx65 (Seq. ID Nos. 9 and 10), Sa163 (Seq. ID Nos. 11 and 12), Ec107 (Seq. ID Nos. 19 and 20), Ec67 (Seq. ID Nos. 13 and 14), Ec86 (Seq. ID Nos. 15 and 16) and Ec73 (Seq. ID Nos. 17 and 18). (Ann. Rev. Microbiol., 5,163-186 (1991)) (H) Structure of hybrid DNA-RNA msDNA-Ye117 (SEQ. ID. NOS. 13 and 14) is shown.

Figure 3:
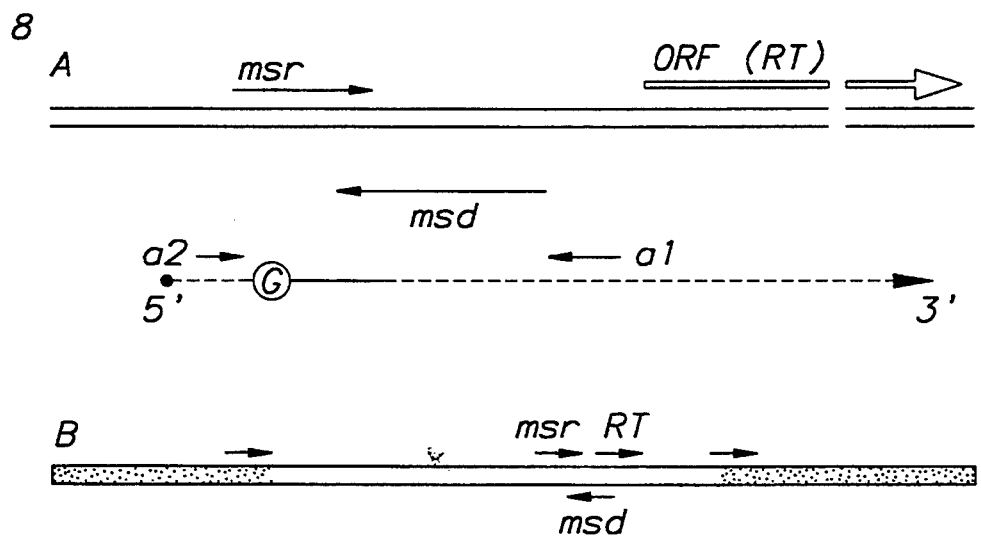
FIG. 3 shows the arrangement of genes in the retro-element responsible for the production of msDNAs.
Figure 8A:
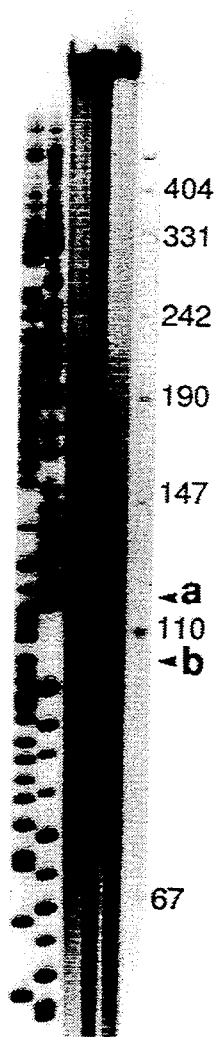
FIG. 8A shows bands a and b of a sequence polyacrylamide gel for the production of msDNA-Ec67 and FIG. 8B shows a schematic representation of extension of the 3' end of msDNA by AMV-RT and RNase A treatment.

FIG. 3 Arrangement of genes in the retron element responsible for the production of msDNA. A single-copy retroelement on the bacterial chromosome contains the region required for the production of msDNA. All known msDNA coding regions contain three genes organized in a similar manner, as shown in (A): A gene, msd, codes for the DNA strand of msDNA. A second gene (msr) is situated, 5' to 3', in the opposite direction and codes for the RNA strand of msDNA. A closely positioned ORF codes for the RT. Transcription of this region initiates at or near the 5' end of msr and extends beyond msd to include the ORF. A set of inverted repeat sequences, a1 and a2, is also conserved among msDNA coding regions (short arrows). The circled G corresponds to the residue in the RNA that will contain the 2',5'branch linkage in msDNA (see also FIG. 8A.). (B) For the E. coli retron Ec67, the region encoding msDNA is only a small part of a large element found on tile chromosome (open bar). The junction of the Ec67 retron with the host chromosome is flanked by 26-base directly repeated chromosomal sequences, as shown by arrows. The Figure is not drawn to scale.

Figure 4:
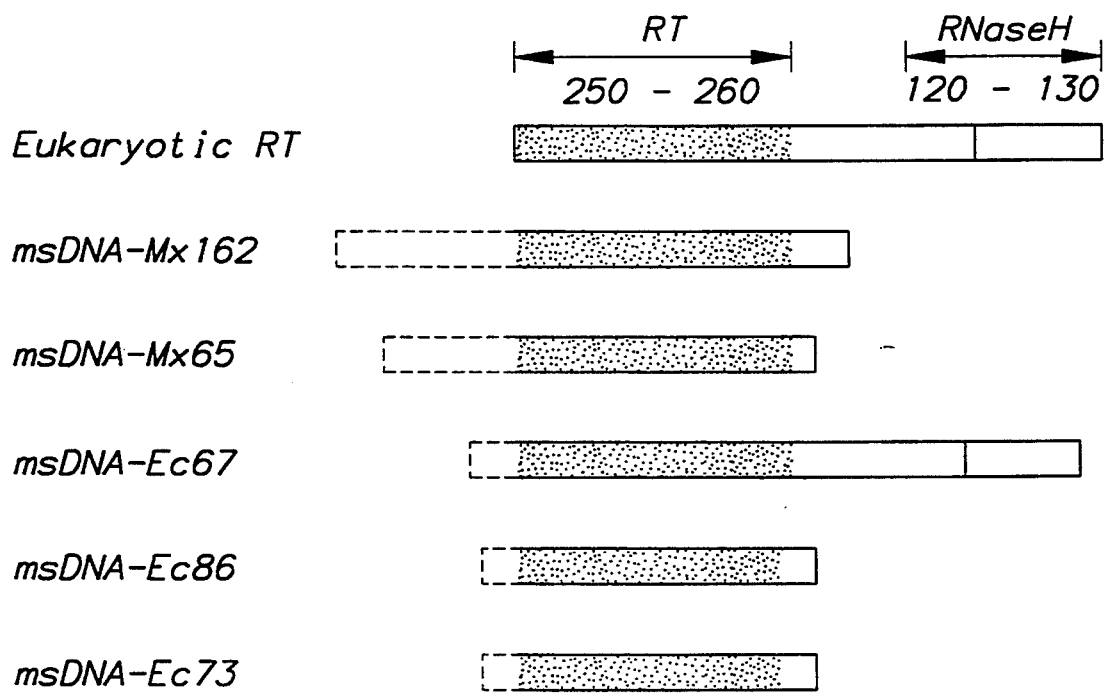
FIG. 4 shows a comparison of the domain structures of various bacterial RTs.

FIG. 4 Domain structures of various bacterial RTs. The regions with closed bars and with stippled bars represent the RT and RNase H domains, respectively.

Figure 5A:
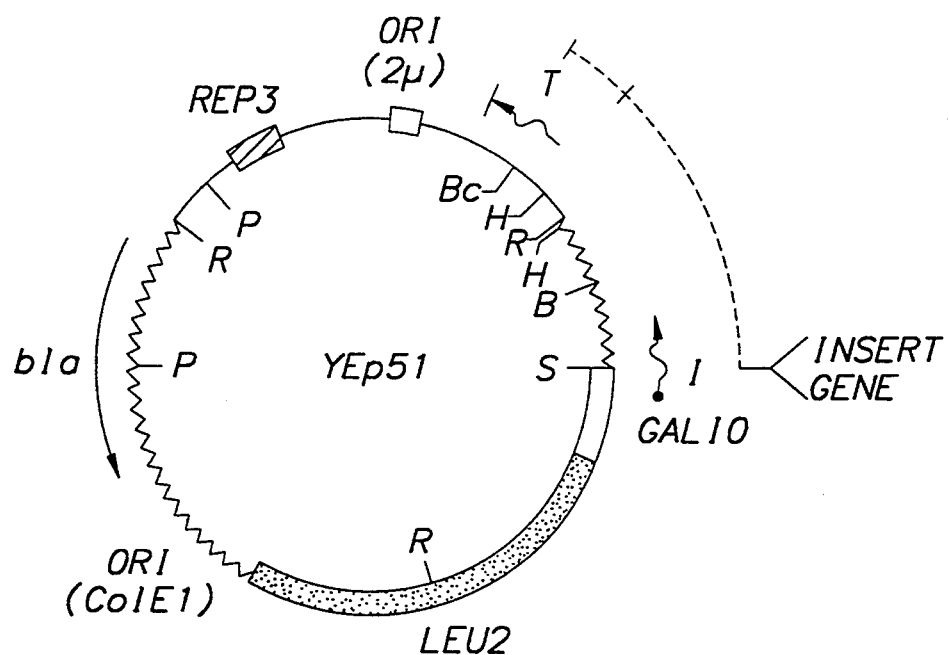
FIG. 5A shows plasmid YEp51 and FIG. 5B shows plasmid YEp52.
Figure 5B:
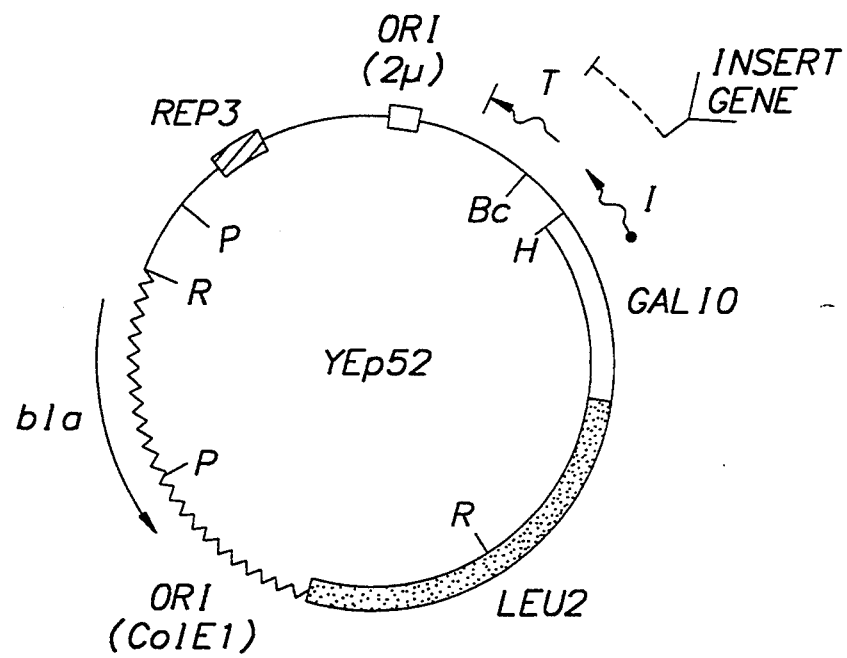

FIG. 5 (A and B) Yeast expression vectors YEp51 (7.3-kb) and YEp52 (6.6-kb). The structures of two yeast expression vectors are diagrammed. Both are composed of sequences from the yeast plasmid 2-μm circle (smooth single line) spanning REP3 (▭) and the origin of replication (▬), from the bacterial plasmid pBR322 (jagged single line) spanning the ColE1 origin of replication and the gene conferring ampicillin resistance, from the yeast genome spanning the gene LEU2 (▭), and from the region 5' to the yeast GAL10 gene (▭), extending from the Sau3A site at −495 from the transcription-initiation site to the SalI site present in plasmid pNN78-Δ4 at +13. A cloned gene inserted in YEp51 in the SalI, SalI-to-BamHI, SalI-to-HindIII, or SalI-to-BclI sites pointed labelled I in the Figure, terminating at a site in the 2-μm-circle sequences indicated by the blocked arrow (T). Similar transcription would be obtained with genes inserted in the HindIII or HindIII to BclI sites of YEp52. Restriction enzymes: R, EcoR1; H, HindIII; B, BamHI; S, SalI, P, PstI; Bc, BclI. See Broach et al., Experimental Manipulation of Gene Expression, Academic Press Inc., New York, 1983.

Figure 6:
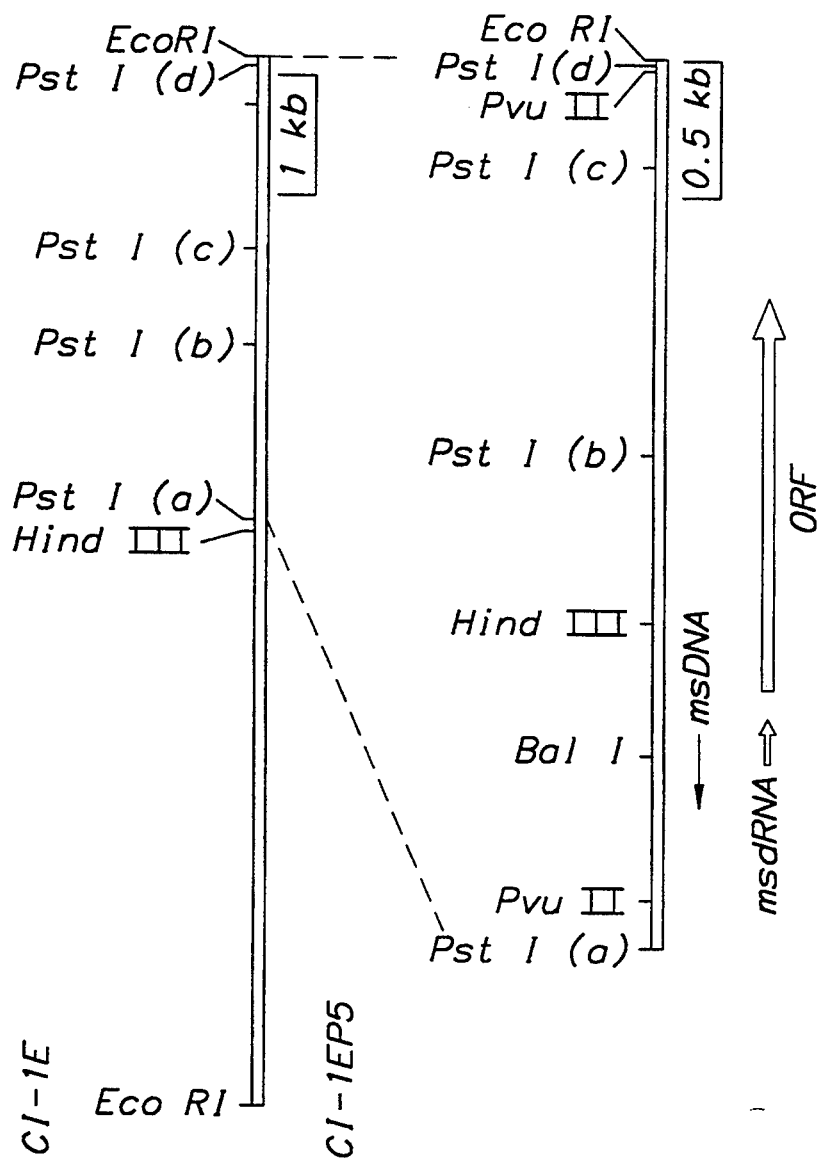
FIG. 6 shows the restriction map of the 11.6-kb EcoR1 fragment.

FIG. 6 Restriction map of the 11.6-kb EcoRI fragment. In the Cl-1E map, the left-hand half (EcoRI to HindIII) was not mapped. In the Cl1EP5 map, the locations and the orientations of msDNA and msdRNA are indicated by a small arrow and an open arrow, respectively. A large solid arrow represents an ORF and its orientation. See Lampson et al., Science, 243, 1033–1038 (1989).

Figure 7:
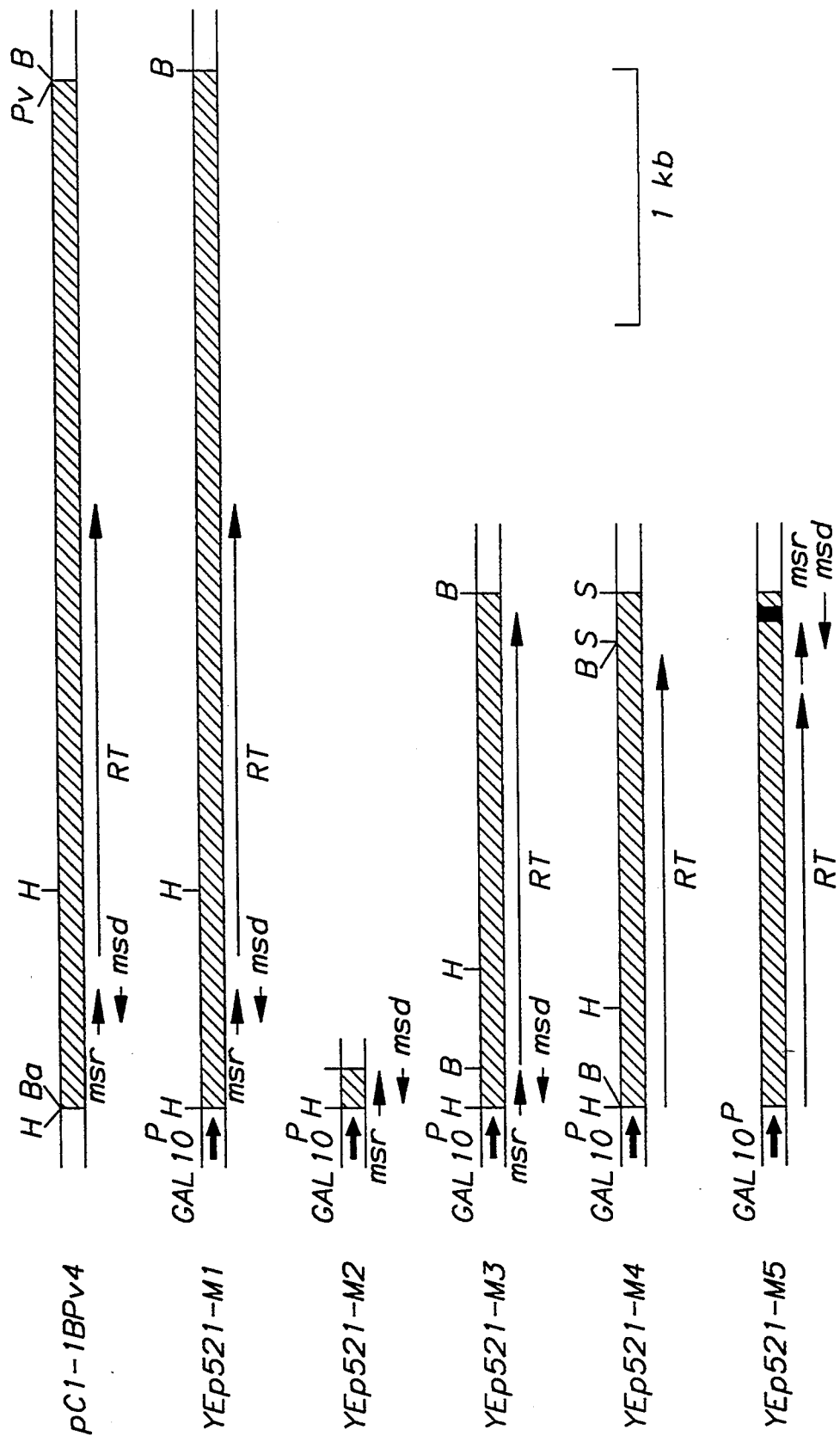
FIG. 7 shows a diagrammatic representation of plasmid PC1-1BPv4, YEp521-M1, YEp521-M2, YEp521-M3, YEp521-M4 and YEP521-M5.

FIG. 7 Diagrammatic representation of plasmid PC1-1BPv4, YEp521-M1, -M2, -M3, -M4 and M-5. Diagrams show only the regions (shaded bars) inserted in the yeast vector, YEp521. These regions contain retron-Ec67 and restriction sites shown are only those which are used for the construction of plasmids. Short arrows with msr or msd are the locations and the orientations of msdRNA and msDNA. Long arrows with RT represent the gene for RT and its orientation. Thick arrows represent the GAL10 promoter and its orientation of transcription. Letters on top of bars are the sites of restriction enzymes: H, HindIII; Ba, BalI; Pv, PvuII; B, BamHI; and S, SmaI.

Figure 8B:
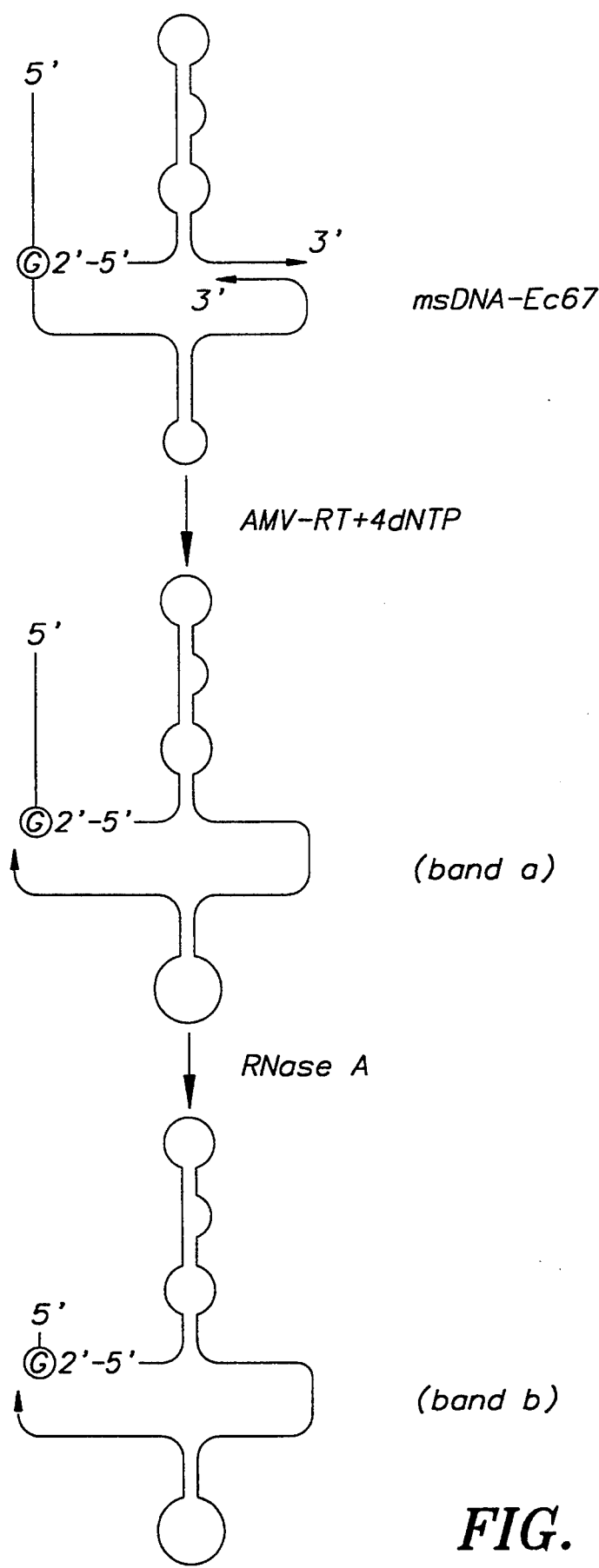

FIG. 8 A sequence polyacrylamide gel of the production of msDNA-Ec67 in S. cerevisiae.

(A) Total RNA prepared from 0.9 ml of a late-log culture was used for detecting msDNA with AMV-RT as described herein below. The RT reaction mixture was subjected to electrophoresis on a 6% sequence-urea-gel. An aliquot of the reaction mixture was treated with RNase A prior to gel electrophoresis. Lanes 1 and 2 (G and C lanes, respectively) are DNA sequence ladders of pUC19 sequenced by chain termination method (Sanger et al., *Proc. Natl. Acad. Sci. USA*, 74, 5463–5467 (1977) ) for size marks; lane 3, the AMV-RT products with total RNA from yeast cells harboring YEp521-M1; lane 4, the same sample as lane 3 except that it was treated with RNase A prior to gel electrophoresis; lane 5, the AMV-RT products with total RNA from yeast cell harboring YEp521. The sample was treated with RNase A. Lane 6 is an MspI digest of pBR322 labeled with [γ−$^{32}$P]dCTP with the Klenow fragment of DNA polymerase I. Numbers at the right-hand side indicate fragment sizes in base pairs and arrows with letters indicate positions of msDNA.

(B) Schematic representation of extension of the 3' end of msDNAEc67 by AMV-RT and RNase A treatment.

Figure 9:
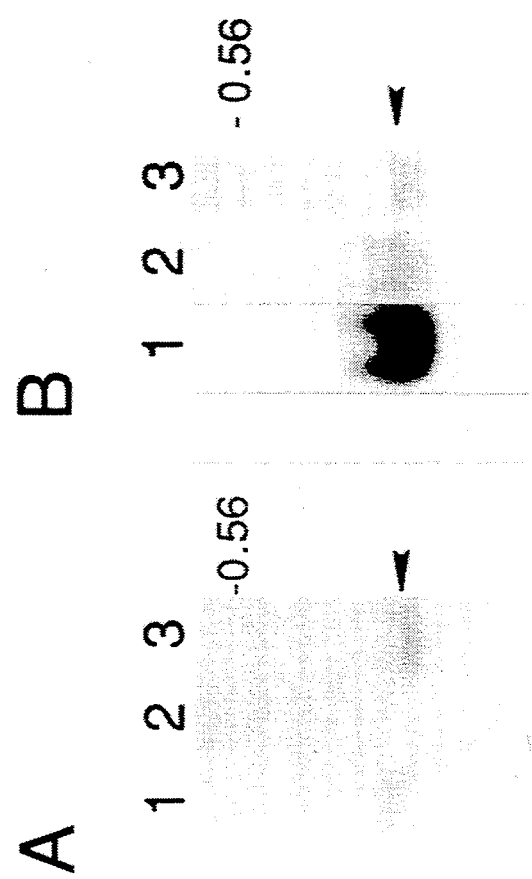
FIG. 9 shows Southern blot hybridization of msDNA-Ec67 produced in S. cerevisiae.

FIG. 9 Southern blot hybridization of msDNA-Ec67 produced in *S. cerevisiae*.

(A) Total RNA fractions prepared from a 2.5 ml culture of yeast cells harboring YEp521-M1(lane 1), and YEp521-M2 (lane 2) and from *E. coli* CL83 harboring pCL-1EP5c (lane 3) were used. After blotted to the nylon membrane filter, msDNA-Ec67 was detected with the nick-translated 140-bp msr-msd DNA fragment as a probe. An arrowhead indicates the position of msDNA-Ec67.

(B) Production of msDNA-Ec67 in *S. cerevisiae* harboring YEp521-M1, -M3, and -M4. Total RNA fractions prepared from a 2.5 ml culture of yeast cells harboring YEp521-M1(lane 3), -M3 (lane 2), and -M4 (lane 1) were used for Southern blot hybridization as described in (A). An arrowhead indicates the position of msDNA-Ec67.

Figure 10:
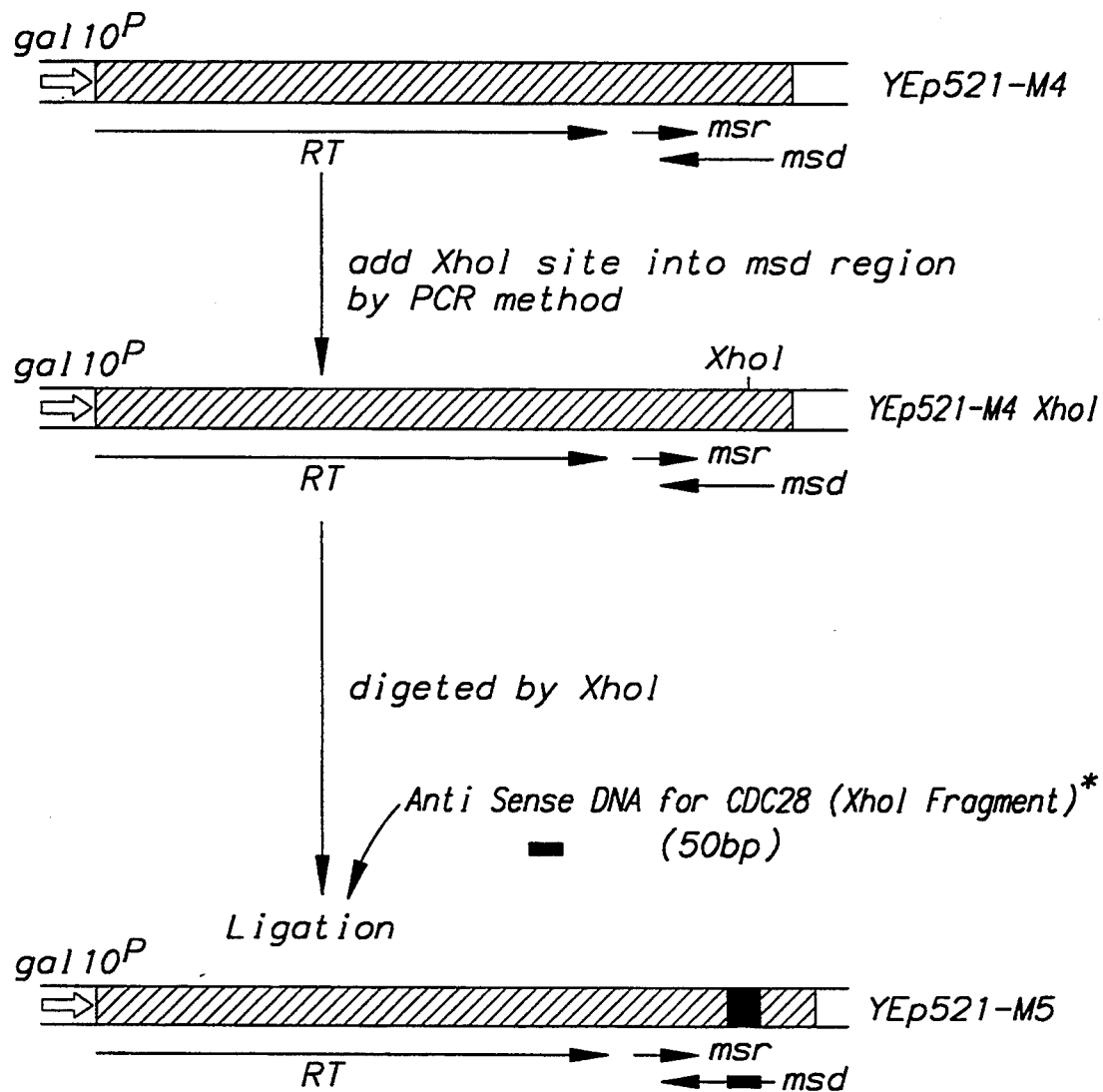
FIG. 10 shows a diagrammatic representation of plasmid YEp521-M5. Darkened region in the retron represents 50-bp antisense DNA for cdc28 (cloned into the XhoI site) inserted into the msd region of retron Ec67. Also shown is the 50-bp antisense DNA for cdc28 (Seq. ID Nos. 1 and 2).

FIG. 10 YEp521-M5 was constructed from YEp521-M4 by inserting into the msd region an XhoI site and into that site, cloning a 50-bp extraneous (foreign) dsDNA fragment which is complementary to mRNA of cdc28 (SEQ. ID. NOS. 1 AND 2). The XhoI site was added into the msd region of YEp521-M4 by PCR. This construct was then digested by XhoI; then the antisense DNA was ligated into the msd region of retron Ec67. This plasmid was transformed into yeast (SP-1) and the subsequently expressed msDNA designated herein as msDNA-Ye117. This is a novel structure.

DETAILED DESCRIPTION OF ILLUSTRATIVE EMBODIMENTS OF THE INVENTION

In accordance with this invention, it has been discovered that a transfected yeast, *Saccharomyces cerevisiae*, produces a genetic structure, described as a synthesized, branched RNA-linked multicopy single-stranded DNA (msDNA). One such msDNA produced was msDNA-Ec67. msDNA-Ec67 was synthesized from retron-Ec67.

The production of other representative msDNAs is described.

Several msDNAs have been described in the literature. Some of these are the following: Mx162 (Dhundale et al., *Cell*, 51, 1105–1112, 1987); Mx65 (Dhundale et al., *J. Biol. Chem.*, 263, 9055–9058, 1988b); Sa163 (Furuichi et al., *Cell*, 48, 47–52, 1987a and Furuichi et al., *Cell*, 48, 55–62, 1987b); Ec67 (Lampson et al., *Science*, 243, 1033–1038, 1989b); Ec86 (Lim and Maas, *Cell*, 56,891–904, 1989); Ec73 (Sun et al., *J. Bacteriol.*, 173, 4171–4181, 1991); Ec107 (Herzer et al., *Mol. Microbiol.*, submitted, August 1991); msDNA from *E. coli*B (Lira and Maas, *Cell*, 6, 891–904, 1989).

References 2, 3, 9 and 14 herein cited are attached to and co-filed with this patent application and are incorporated herein by reference.

The msDNAs. The msDNAs are often referred to in the literature by a numeral preceded by a suffix indicating a host origin. For instance, "Mx" referring to *Myxococcus xanthus*, and "Ec", referring to *E. coli* and "Sa" to *Stigmatella aurantiaca*.

msDNAs are unique molecules which in spite of extensive diversity, share similar structural features. Generically, msDNA may be described as being a molecule which comprises a branched RNA which is covalently linked to a single-stranded DNA by a 2',5'-phosphodiester bond between the 2'—OH group of an internal rG residue and the 5'-phosphate of the DNA molecule, and which RNA is non-covalently linked to the DNA by base pairing between the complementary 3' ends of the RNA and DNA molecules, which RNA and DNA form the stable stem-loop secondary structures. The msDNA molecule is encoded by a primary RNA transcript, pre-msDNA, which contains an open-reading frame (ORF) downstream of the msr locus encoding a polypeptide which has sequence similarity with retroviral RTs and a highly conserved sequence common to RTs.

The pre-msDNA may alternatively contain its ORF upstream of the msr locus, in which event the retron will be of like construction.

In FIG. 2 (A–G) which shows typical msDNAs, the RNA portion of the molecule is shown "boxed"; the balance of the structure being the ssDNA portion.

It will be noted that the molecules all show a branched rG residue, a DNA-RNA hybrid at the 3' ends of the msDNA and msdRNA, and a stem-loop structure in the RNA and DNA strands. The branching ribonucleotide, G, is circled and the 2',5'-phosphodiester linkage to the first deoxynucleotide is indicated.

Retrons. A retron is a small genetic element to date found to be of 1.3 to 2.5-kb in length constituted of an msr-msd region and by the gene for encoding reverse transcriptase (RT). The coding region for msDNA is indicated by "msd"; the coding region for msdRNA is indicated by "msr".

A comparison of all known msDNA coding regions reveal that this locus contains three genes organized in a similar manner. See FIG. 3. A gene called msd codes for the DNA portion of msDNA. A second gene, msr, is situated 5' to 3', in the opposite orientation of msd, and codes for the RNA chain. Thus the genes msd and msr are covergently oriented so that their respective 3' ends overlap by several bases.

This overlap is equivalent to the H-bonded DNA-RNA structure formed by the overlapping 3' ends of the RNA and DNA strands in the msDNA molecule. For Mx162, the overlapping msd-msr genes, like the hybrid structure of the msDNA they produce, comprise 8 base pairs. See Table I for typical overlap lengths of various msDNAs.

Determination of the nucleotide sequence in the vicinity of the msd-msr genes revealed a closely-linked open reading frame (ORF). This ORF is located immediately upstream from msd, but is transcribed in the same direction as msr (as shown in FIG. 7). The initiation codon of the ORF is situated as close as 19 basepairs from the start of the msd gene for the Ec86 retron of *E. coli* B, but as much as 77 base-pairs for the Mx162 retron of *M. xanthus*.

Another conserved feature of the chromosomal locus that codes for msDNA is a set of inverted repeat sequences, designated a1 and a2. Sequence a1 is located just upstream from the start of the msd gene, while sequence a2 is positioned immediately 5' to the G residue in the msr gene that forms the 2',5' branch linkage in the msDNA molecule (FIG. 4). The inverted repeats display a large degree of nucleotide sequence diversity among the different known loci encoding msDNA, as well as differences in size. For example, the inverted repeats (a1 and a2) found in the retron locus encoding Mx162 are 34 nucleotides long, while the inverted repeats for the Ec86 retron of *E. coli* B are only 12 bases in size. Despite their diversity, these repeat sequences are located in the same positions (as shown in FIG. 3) for all known loci encoding msDNA. As discussed in more detail below, the position of these inverted repeat sequences is critical to the synthesis of msDNA.

It will be helpful to refer to the above discussion when the aspects of the invention are discussed which provide for an inversion in the organization (position inversion) of the RT gene with respect to the msr-msd coding region, and in the discussion of shortening the non-coding region between the transcriptional initiation site and the initiation codon AUG of the RT gene.

The promoter for the msr-msd region is upstream of msr. Transcription is from left to right, encompassing the entire region including the RT gene. As described in further detail hereinafter, the replicating vehicle for transfecting the eucaryote host may harbor one promoter for the msr-msd and the RT, or it may contain two promoters, one for the msr-msd region and the other for the RT.

It is within the scope of the invention that retrons be constructed to yield an msDNA which differs from the typical msDNAs by features other than the common, conserved and characteristic features of msDNAs described above. For instance, it is not excluded that the length and/or location of the set of IRs a1 and a2 in the retrons be varied providing they remain in the same location discussed above. Thus, the size and/or location of the loops in the stems of the msDNA can be Further, it is not excluded that the extent of or overlap of the base pairing of the 3' ends of DNA and RNA in the msDNAs be influenced (increased or decreased) by appropriate manipulations. Whether such variations will be desirable will depend on the ultimate utility proposed for these msDNAs.

General Features of msDNAs. Table I is a summary of the structure of representative retrons.

Reverse Transcriptase (RT). The domain structures of bacterial RTs of representative retrons are shown in FIG. 4.

The RT gene is normally located downstream from the msr-msd region. In the new retrons which differ from the bacterial retrons, their relative positions are reversed, the msr-msd region is located downstream of the RT gene.

The biosynthesis of msDNAs has been described in Inouye & Inouye, *Ann. Rev. Microbiol.*, 45, 163–186 (1991b) and Herzer et al., *Mol. Microbiol.*, submitted, August 1991. A schematic of the synthesis is shown in FIG. 1. A primary transcript (pre-msdRNA) is considered to encompass the upstream region of msr through the RT gene, which is by reference to FIG. 1, shown by a thin line at step 1. The thick region in the RNA transcript corresponds to the final msdRNA. The branched G residue is circled, and the initiation codon for RT is also shown. On the folded RNA, a triangle indicates the 5' end processing site at the mismatching base. The dotted lines at steps 3 and 4 represent DNA strands.

In summary, the primary transcript from the msr-msd region is believed to serve not only as a template but also as a primer to produce the msDNA. Synthesis of msDNA is primed from an internal rG residue of the RNA transcript using its 2'-OH group. Thus, msDNA is branched out from this rG residue by a 2'-5'-phosphodiester linkage.

There will be described hereinafter the transformation of yeast cells harboring plasmids which contain a retron (which includes the RT gene) for expression of the desired msDNAs. The description is of a best mode to date to express msDNA-Ec67 from its retron, Ec67.

1. Synthesis of msDNA-Ec67. For the expression of msDNA-Ec67, plasmid YEp52 was used. Plasmid YEp521 was constructed by introducing the multiple cloning sites of pUC19 (Yanisch-Perron et al., *Gene*, 33, 103–119, 1985) into YEp52, which was designed to obtain high-level, inducible expression of a cloned gene under the GAL10 promoter in yeast. YEp52 contains the ColE1 origin of replication (OR), a promoter of the GAL10 gene, LEU2, the 2μ-circle origin of replication, and the 2-μ circle REP3 locus. See FIG. 5(A and B). See Broach et al., *Experimental Manipulation of Gene Expression*, Academic Press Inc., New York, 1983.

Retron-Ec67 was prepared from plasmid pCL-1BPv4 in which the 4-kb BalI-PvuII fragment (DNA from fragment from the BalI to 2nd PvuII site from the left end of the map depicted in FIG. 5(A and B) was cloned into the HincII site of pUC9. *E. coli* harboring this plasmid produces msDNA-Ec67 (Lampson et al., *Science*, 243, 1033–1038, 1989).

A total RNA fraction was prepared from cells transfected with pCl-1EP5c; pCl-1EP5c contains the 5-kb PstI(a) -EcoRI fragment encompassing the entire 4-kb BalI-PvuII sequence in PCl-1BPv4. See FIG. 7.

The construction of plasmid YEp521 proceeded as follows. The DNA fragment containing the pUC19 multiple cloning sites were isolated by digestion of pUC19 with EcoRI, the cleaved ends were filled in with the Klenow fragment of DNA polymerase I, and then digested with HindIII. The resulting 54-bp fragment was cloned into YEp52 by replacing a fragment between the BclI (filled in with the Klenow fragment) and HindIII sites, resulting in YEp521.

YEp521, thus constructed, contains the multiple cloning sites from pUC19, except for EcoRI, downstream of the GAL10 promoter.

The 4-kb HindIII-BamHI fragment from pCl-1BPv4 (see FIG. 7) was cloned into the HindIII and BamHI sites of YEp521.

As a result, the msr-msd region and the RT gene of retron-Ec67 were placed downstream of the GAL10 promoter. This plasmid is designated YEp521-M1.

Plasmid YEp521-M1 is illustrated in FIG. 7. The shade bars are the regions inserted in yeast vector, YEp521.

It will be noted that the RT of retron-Ec67 gene is located behind (downstream) the msr-msd region.

2. Production of msDN A in transformed yeast. A yeast strain ( SP1, a vra3 leu2 trp1 his3 ade8 can ga12) was used. Transformation of the yeast cells was carried out by the lithium acetate method of (Ito et al., *J. Bacteriol.*, 153,163–168, 1983). Yeast culturing was carried out as described below msDNA was produced and was detected by extending the 3' end of msDNA by avian myeloblastosis virus reverse transcriptase (AMV-RT). This yielded a main product of 117 nucleotides. Treatment of this product with ribonuclease A resulted in a DNA of 105 nucleotides. These results are in good agreement with the structure of msDNA-Ec67. (See Lampson et al., Science, 243, 1033–1038, 1989). The production of msDNA-Ec67 was further conformed by Southern blot hybridization.

To determine whether the production of msDNA-Ec67 could occur in yeast without the RT genes from retron Ec67, the following work was performed.

An RNA preparation from cells harboring YEp521-M2 only contains the msr-msd region under the GAL10 promoter, and described herein above (See FIG. 7) was analyzed by Southern blot hybridization. As shown in lane 2, FIG. 9, no band corresponding to msDNA-Ec67 was detected, indicating that the RT gene from retron-Ec67 is essential for the msDNA synthesis in yeast cells.

In a similar manner, CHO cells can be transformed using known strategies and techniques. The same could be done with HeLa cells or other vertebrate mammalian cells.

Gene Rearrangement in Retrons. An important finding in connection with the invention is that the yield of msDNA in transfected yeast cells is significantly improved by means which cause, it is believed, an increase in production of RT. One such strategy is to reduce by as many as possible the numbers of the AUG codons between the transcriptional initiation site of the GAL10 promoter (or any other promoter used for that purpose) and the initiation codon of the RT gene. Best results were obtained when a portion of the 5' end non-coding region containing initiation translation codons AUG is deleted, but for the first AUG codon in closest proximity to the 5' end.

Thus, it was found that a significant portion of the 5' end of the non-coding region was not essential to production of msDNA in yeast cells. Deletion of a portion of the nucleotide sequence containing the AUG codons significantly improved the yield of msDNA production.

Specifically in YEp521-M1(See FIG. 7 ), there are 417-bp from the 5' end HindIII site to the initiation codon GAA for RT. (See FIG. 7 in Lampson et al., Science, 243, 1033–1038, 1989). A deletion of the 240-bp sequence upstream of the msr gene from the left hand most HindIII site to immediately upstream of msr of YEp521-M1( See FIG. 7 ) was carried out.

For this purpose, the fragments of 140-bp msr-msd (including 5 extra bases upstream of msd and 18 extra bases at the 3' end of the msr-msd region upstream of msd) (after PCR amplification) and the 1.8-kb RT gene (including 8 bases upstream) of the initiation codon of the RT gene (also after PCR amplification) (and 4 bases downstream of the termination codon), were cloned into the HindIII and BamHI sites of YEp521-M1yielding YEp521-M3 (See FIG. 7). The yield of msDNA-Ec67 in transfected yeast with YEp521-M3 was shown to be significantly increased, as discussed below.

Another important finding made to substantially increase the yield of msDNAs in yeast is to transpose the position of the RT gene with respect to the msr-msd region. In bacterial retrons, the msr-msd region is in front of the RT gene; when the RT was moved upstream of the msr-msd region, a further increase in yield of msDNA was observed. This was accomplished as follows.

Since the msr-msd region of YEp521-M3 still contains 3 AUG codons, YEp521-M4 (See FIG. 7) was constructed, in which the order of the RT gene and the msr-msd region was reversed, i.e., the msr-msd region being positioned after the RT gene. In YEp521-M4, there is only one AUG codon between the left hand-most HindIII site and the BamHI site (See FIG. 7), which exists in the multiple cloning sites of PUC19. (Yabisch-Perron et al., Gene, 33,103–119, 1985). This AUG codon is terminated by a termination codon, UAG after 5 codons. The initiation codon, GAA, for the RT gene was placed 6 codons after the termination codon in the same reading frame.

YEp-M5 was then constructed from YEp521-M4 by adding 50-bp antisense DNA for cdc28 into the region coding for msd (described in further detail below). Therefore, two plasmids were constructed in which the order of the RT gene and the msr-msd region was reversed.

The yield of msDNA-Ec67 in transfected yeast cells with YEp521-M4 was compared between YEp521-M4 and YEp521-M3. This gene rearrangement brought about a further increase of yield over YEp521-M3. The msDNA production was increased approximately 1.2 and 9.4-fold with YEp521-M3 and YEp521-M4, respectively, over YEp521-M1.

It has been reported that a ribosomal subunit (carrying Met-trNA$^{met}$ and various initiation factors) binds initially at the 5' end of mRNA and then scans through the mRNA stopping and then initiates translation at the first AUG codon in a favorable context (Kozak, J. Cell Biology, 108,229–241, 1989). From a recent survey of 699 vertebrate mRNAs, a consensus sequence for initiation of translation in higher eucaryotes has been identified (Boeke et al., Cell, 40, 91–500, 1985). The survey reports the study of the 5' non-coding sequences of the 699 vertebrates mRNAs (all sequences to which access could be had in the literature). The mRNA source of the vertebrates included human, (muscle, skeletal, liver, intestinal, etc. ) bovine, rat and others. Also in yeasts, AUG was reported to be the consensus of sequence for initiation of translation. (Hamilton et al., Nucl. Acids Res., 15, 3581–3583, 1987) It is noted that Kozak, J. Cell Biology, 108,229–241, 1989 also reported variations and exceptions to the more general rule described above. For instance, there are reported cases where initiation is not restricted to first AUG codon, which therefore is not used exclusively, but includes other AUG codons in the vicinity of the 5' end. Further, inactivating the first AUG codon closest to the 5' end, allowed ribosomes to initiate translation at another codon (UUG).

As described herein above, the location of the initiation codon of the ORF for various msDNAs can vary (e.g., 19-bp from the start of the msd gene for Ec86 retron and 77-bp for the Mx162 retron). Thus, one skilled in the art can adjust the length of the excised non-coding region of the retron when the above strategy is followed.

The finding in connection with the invention described above, namely, that a significant improvement in yield of msDNAs takes place when AUG codons between the transcriptional site of the GAL10 promoter and the initiation codon of the RT gene are deleted, but for the one AUG codon closest to the 5' end which is preserved, is therefore consistent with the above-discussed literature reports. Accordingly, this finding made in accordance with the invention with respect to the production of msDNAs is not intended to be limited to yeast, but can reasonably be predicted to apply to other msDNA-producing transfected eucaryotes, in particular higher eucaryotes like mammalian cells, e.g., HeLa cells, CHO, COS-1 cells and others.

The same observation can be made regarding the position of the RT gene upstream of the msr-msd region. This finding too is believed to have general applicability to the production of msDNAs in eucaryotes, as noted above. It is believed that these described strategies may contribute to an increase in RT and ultimately in yield of msDNAs.

It will be apparent to one skilled in the art that the two strategies described (deletion of AUG codons and inversion of the respective positions of the RT gene and the msr-msd region, do not have to be performed together (as shown with respect to YEp521-M4), which is a best mode to date. For instance, the strategy may be performed without the deletion strategy, and vice-versa. Further, as noted above, any strategy which will contribute to the increase of the production of RT, is considered within the scope of the invention.

The msDNAs which are synthesized from these new retrons are also new.

As has been noted herein, it is not necessary that one promoter for the RT gene and the msr-msd region be used. More than one can be used, one for the RT and one for the msr-msd region. When it is desired to use two promoters, either one or both of the strategies to increase RT production namely the inversion and/or deletion strategy can also be used, as will be apparent to one skilled in the art.

It is noteworthy that the DNA sequences, which contain these unique retrons (due to the deletions and/or position inversion) and which encode the new msDNAs, are new when compared to known bacterial retrons. So are the replicating vehicles carrying these retrons and the transfected eucaryotes harboring these vehicles. They provide effective means to produce new single-stranded DNA in eucaryotes in improved yields.

It is to be noted also that the two above-described strategies which have been discussed with respect to eucaryotes are applicable to msDNAs produced from modified retrons in procaryotes.

The invention has been illustrated with an illustrative retron, Ec67. However, by a similar procedure, yeast can be made to produce other msDNAs. For instance, in a similar manner, retron Ec73 can be used to transform yeast strain SP1 to produce msDNA-Ec73.

Likewise, a similar procedure can be followed to transform and produce msDNA-Mx65 in yeast from the necessary retron elements. See Dhundale et al., *JBC*, 263, 9055–9058, 1988. Its ORF codes for 427 amino acid residues.

If it is desired to produce msDNA-Mx162 in yeast, the appropriate DNA fragment containing retron Mx162 can be prepared from a 17.5-kb SalI fragment which is disclosed in Tee et al., *Cell*, 38,203–209, 1984. Its ORF codes for 485 amino acid residues.

For the expression of msDNA-Ec107, a similar strategy may be followed. The retron is a 1.3-kb DNA fragment of which the 34-bp intergenic sequence to between pyrE and ttk (in FIG. 4) is deleted. The retron contains an ORF coding for 319 amino acid residues (from base 396 to 1352 in FIG. 2)(A–G). The reference to Figures made hereinabove is to Dhundale et al., *Cell*, 51, 1105, 1987. This retron is the smallest yet found in bacteria.

The retron for Sa163 was determined to be contained in a 480-bp DNA fragment encompassing the msd and msr regions (Furuichi et al. ).

The retron for Ec73 was determined to be contained in a 3.5-kb SalI(b)-EcoRI(c) fragment. See FIG. 1A of Sun et al.. For details on Ec73, see below.

The retron for Ec86 was determined to be contained in a 3.5-kb PstI fragment (Lim and Maas, *Cell*, 56,891–904, 1989).

Likewise, from retrons Sa163, Ec86 and Ec73, the corresponding msDNAs, msDNA-Sa163, msDNA-Ec86 and msDNA-Ec73 may be produced in transfected yeast cells. If plant or mammalian vertebrate cells are used, appropriate manipulations and strategies will be followed.

Similar techniques may be followed to express other msDNAs known or yet to be found or to be synthesized from their respective retrons. All of these retrons are expected to contain the elements necessary to synthesize the unique features of msDNAs, as is described herein.

Thus, in general retrons containing the essential features described herein are useful to produce in vivo in eucaryotes the stable (not degraded) msDNAs having the conserved and characteristic features described herein.

msDNA-Ec73 is synthesized from retron Ec73 which is described in Sun et al., *Journal of Bacteriology*, 173, 4171–4181, 1991. This reference is incorporated by reference. FIG. 2 therein shows the nucleotide sequence capable of synthesizing msDNA-Ec73, a 3.5-kb S(b)-E(c) fragment. It was determined that the first ATG codon at position 11,544 is the initiation for the necessary RT gene and the ORF for the RT is of 316 residues.

It is to be noted that in all retrons known to date, the RT gene is located at 20 to 77-bp upstream of the msd gene (downstream of the msd gene).

In all retrons studied to date, it is believed that the promoter elements serve as the promoters for both msdRNA synthesis and the ORF. For instance, for msDNA-Ec67, promoter elements in a $-10$ region TTGACA and in a $-35$ region TGAAT, are believed to fulfill this function. See Lampson et al., *Science*, 243, 1033–1038, 1989. However, in accordance with the invention, it is not essential that there be one promoter element for both components, but rather two promoter elements, one for initiating RNA polymerase transcription for the RT gene and the other for the msr-msd region. Thus the msr-msd region and the RT gene can be expressed under two independent promoters, which would be likely to complement each other. However, it appears at this time that at least for two of the msDNAs described herein (msDNA-Ec67 and msDNA-Ec73), the production of msDNA-Ec67 can only be complemented by the RT-Ec67 and not by the RT-Ec73 or vice-versa.

Further, it is often desired to use a strong promoter rather than the native promoter.

Another important embodiment of the invention relates to the in vivo production in eucaryotes of any DNA fragment(s), non-native or foreign, to the msDNA structure. Likewise, the vectors and the transfected eucaryotic hosts, carrying such foreign DNA fragment(s) are encompassed by the invention. The invention thus makes possible the synthesis in vivo in eucaryotes of stable msDNAs which encompass a foreign DNA fragment in the DNA portion or a foreign RNA fragment in the DNA portion of the DNA-RNA hybrid structure. Of particular interest are msDNAs which include a single-strand or DNA or RNA fragment which is complementary to the mRNA of a particular target gene (or fragment) thereof (antisense DNA or RNA).

In one example of this embodiment, there was constructed a plasmid, YEp521-M5, into which there was inserted in the msd region, nucleotides 299-426 of YEp521-M4 (the boxed region of the lower strand of FIG. 7 of Lampson et al., Science, 243, 1033-1038, 1989), a XhoI restriction recognition of site (T ↓ CTAG)); a foreign DNA fragment of 50-bp was inserted in this XhoI site. YEp521-M5 was transformed into yeast (SP-1) and the subsequently expressed msDNA designated herein as msDNA-Ye117 (Seq. 1D. Nos. 13 and 14) (see FIG. 2).

In a like manner, there may be inserted into the msr region of YEp521-M4 a restriction recognition site, and into a DNA fragment. This retron may be transformed into yeast (SP-1), and the subsequently expressed msDNA is a new structure. It corresponds to the structure designated here as msDNA-Ye117, (Seq. 1D. Nos. 13 and 14) except that the new foreign fragment is in the RNA portion of the msDNA.

The invention makes possible the construction of a system that may be used to regulate the production of genes. The modified msDNAs of the invention contain in the DNA portion, a clone DNA fragment from a gene downstream of a promoter in the orientation promoting the production of antisense DNA or RNA (micRNAs). The "micRNA" terminology has been applied to an RNA transcript which is an mRNA-interfering-complementary RNA (Coleman et al., Cell, 37, 429–436 (1984) and literature references cited therein). "micRNA" has been reported to inhibit the production of certain proteins (e.g., OmpF). A similar regulation has been reported for a micRNA and the gene for the Tn10 transposase gene. The gene for the micRNA and for the transposase are reported to be transcribed in opposite directions off the same segment of DNA, such that the 5' ends of their transcripts can form a complementary hybrid. The hybrid is thought to inhibit the translation of the transposase mRNA. Coleman et al., supra., report the construction of an artificial "mic" system designed to regulate the expression of any specific gene in E. coli.

Various cell division cycle (cdc) genes are known; by now some 50 different cdc genes have been defined in terms of landmark events occurring during duplication of cellular molecules (e.g., glycolic events). Various cdc genes and their functions are described in Watson et al., Molecular Biology of the Gene, Fourth Ed. (1987), Chapter 18. Amongst these are cdc4 required for initiation of DNA synthesis in the mitotic cell division cycle and other functions; cdc7 of similar function to cdc4 but for premeiotic DNA synthesis; cdc28 necessary for duplication of the spindle pole body is homologous to mammalian protein kinases and has protein kinase activity, and others like cdc8, cdc9 and others.

The strategy to produce a msDNA containing a foreign dsDNA fragment in its DNA portion is depicted in FIG. 10. The DNA fragment is shown (dark bar). The 50-bp nucleotide fragment (Seq. 1D Nos. 1 and 2) is shown below with

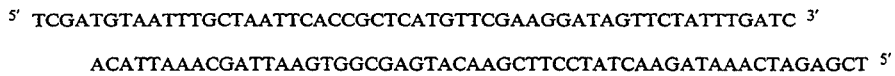

Yeast cells (SP-1) transfected with YEp521-M5 produced a new msDNA-like structure, msDNA-Ye117, (Seq. 1D. Nos. 13 and 14) shown in FIG. 2B (analyzed by polyacrylamide-urea gel electrophoresis). This new msDNA construct contains the 50-bp DNA fragment. It is contemplated that the new msDNA is a useful vector for antisense DNA. The new construct is expected to produce a single-stranded DNA which is complementary to a specific mRNA, in this instance, that of cdc28 and inhibit the expression of that mRNA, and of the gene.

Antisense DNA (micDNA) and micRNAs which are complementary to regions of the mRNA known to interact with ribosomes, would be of particular interest. Hence, such msDNAs that contain such DNA-micDNA generating regions are of special interest for various applications. Thus, by inserting an appropriate DNA fragment of a gene after a promoter, e.g., into an XhoI site, one can construct with the msDNAs disclosed herein (and others) a system to specifically regulate the expression of any gene.

This is the first time that such antisense system has been provided from a molecule produced in an eucaryote.

It is contemplated that other DNA fragments be inserted in the msd region and/or the msr region of the plasmid here disclosed and the corresponding new msDNAs synthesized which may have similar functions, e.g., to generate a micDNA or a micRNA complementary to a mRNA to inhibit its gene.

Likewise, YEp521-M1 can be modified, producing an enlarged new msDNA structure (on the 5' end of the DNA portion of msDNA).

When it is desired to insert a DNA sequence encoding a protein (polypeptide) e.g., two copies of a gene, the DNA sequence will be inserted in opposite orientation to another at a selected restriction site into the msd sequence of an msDNA of choice, such as YEp521-M4. There is expected to be produced in an eucaryotic host, a novel msDNA-RNA structure. When the lacZ gene is incorporated into a suitable location in the msd region of the selected construct, it is expected that β-galactosidase activity will be detected.

EXAMPLES

The following Examples are offered by way of illustration and are not intended to limit the invention in any manner. In these Examples, all percentages are by weight for solids and by volume for liquids, and all temperatures are in degrees Celsius unless otherwise noted.

For convenience and clarity, the Examples refer to and provide also a detailed description of the Figures.

Example 1

Yeast Strains Media and Growth Condition

Yeast SP1 strain (a ura3 leu2 trp1 his3 ade8 can^r gal2) was used. Cells were grown in YPD medium (1% yeast extract, 2% bactopeptone, and 2% glucose). For screening transformants of YEp52 and its derivatives, a minimal medium was used (Rose et al., *Methods in Yeast Genetics: A Laboratory Course Manual*, Cold Spring Harbor Lab., Cold Spring Harbor, N.Y., 1990), supplemented with all nutrients required but leucine. For galactose induction, 0.15 ml of the pre-cultured cells in the minimal medium containing 2% galactose instead of glucose were utilized. The cells were grown at 30° until late-log phase. Yeast transformations were carried out by the lithium acetate method (6). Transformation of yeast cells was confirmed as follows: the plasmid prepared from yeast transformants was transformed into *E. coli* DH-5 (F⁻ endA1 recA1 hsdR17 (rk⁻,k⁺) supE44 thi-1, gyrA96, relA1) and the plasmid prepared from DH-5 cells was not yet subsequently characterized. Plasmid DNA from yeast cells was prepared according to the method described by Hoffman and Winston, *Gene*, 57, 268–272, 1987.

Plasmids. YEp52 (Broach et al., *Experimental Manipulation of Gene Expression*, Academic Press Inc., New York, 1983) was used to construct plasmids for expression of msDNA in yeast. This plasmid contains the ColE1 origin of replication, a promoter of the GAL10 gene, LEU2, the 2 μ-circle origin of replication, and the 2μ-circle REP3 locus. Retron-Ec67 was prepared from plasmid pC1-1BPv4 in which the 4-kb BalI-PvuII fragment (DNA fragment from the BAlI to the 2nd PvuII site from the left end of the map described in FIG. 5 of Lampson et al., *Science*, 243, 1033–1038, 1989), was cloned into the HincII site of pUC9. *E. coli* harboring this plasmid produces msDNA-Ec67. A total RNA fraction was prepared from cells transformed with pC1-1EP5c. pCL-1EP5c contains the 5-kb PstI(a)-EcoRI fragment encompassing the entire 4-kb Bal-I-PvuII sequence in pC1-1BPv4 (see FIG. 5 of Lampson et al., *Science*, 243, 1033–1038, 1989)in pUC9.

Plasmid Construction. Plasmid YEp521 was constructed by introducing the multiple cloning sites of pUC19 (Yanisch-Perron et al., *Gene*, 33,103–119, 1985) into YEp52 (Broach et al., *Experimental Manipulation of Gene Expression*, Academic Press Inc., New York, 1983), which was designed to obtain high-level, inducible expression of a cloned gene under the GAL10 promoter in yeast. The DNA fragment containing the pUC19 multiple cloning site was isolated by digestion of pUC19 with EcoRI; the cleaved ends were filled in with the Klenow fragment of DNA polymerase I, and then digested with HindIII. The resulting 54-bp fragment was cloned into YEp52 by replacing a fragment between the BclI (filled in with the Klenow fragment) and HindIII sites, resulting in YEp521. YEp521, thus constructed, contains the multiple cloning sites from pUC19, except for EcoRI, downstream of the GAL10 promoter. The 4-kb HindIII-BamHI fragment from pC1-1BPv4 was cloned into the HindIII and BamHI sites of YEp521. As a result, the msr-msd region and the RT gene of retron-Ec67 were placed downstream of the GAL10 promoter. This plasmid is designated YEp521-M1 as shown in FIG. 7.

In order to eliminate a fragment of 242 bases upstream of msr which contains several ATG codons, polymerase chain reaction (PCR) was performed using YEp521-M1 as a template with two synthetic oligonucleotides, M2-a(5′GCAAGCTTCATAAACACG-CATGT3′) and M2-b (5′CTGGATCCAGAAACG-CATGCAGG3′) as primers (Seq. 1D Nos. 3 and 4). These sequences correspond to the sequences from base 243 to 258 of retron Ec67 for M2-a and from base 384 to 369 for M2-b (see FIG. 7 of [22]), which flank the msr-msd region. The 140-bp PCR product was gel-purified and digested with HindIII and BamHI. The resulting fragment was cloned into the HindIII and BamHI sites of YEp521, yielding YEp521-M2. YEp521-M2 contains only the msr-msd region under the GAL10 promoter.

To insert the RT gene at the BamHI site of YEp521-M2, the 1.8-kb BamHI fragment encompassing the RT gene was amplified by PCR using YEp521-M1 as a template and two oligonucleotides, M3-a (5′, CTGGATCCAAGAAATGACAAAAACA3′) and M3-b (5′CTGGATCCTTCATTAGCTATT-TAACAT3′) as primers (Seq. ID Nos. 5 and 6), which correspond to base 409 to 429 and from base 2182 to 2163 of retron-Ec67 (see FIG. 7 of Lampson et al., *Science*, 243, 1033–1038, 1989), respectively. The 1.8-kb fragment was gel-purified, digested with BamHI, and closed into the BamHI site of YEp521-M2. The resulting plasmid was designated YEp521-M3.

YEp521-M4 was constructed to change the order of the msr-msd region and the RT gene. The msr-msd region was amplified by PCR using M2-a and M2-b (see above) except that SmaI sites were added at their 5′ ends. The 1.8-kb BamHI fragment containing the RT gene was cloned into the BamHI site of YEp521. Subsequently, the 140-bp SmaI fragment containing the msr-msd region was cloned into the SmaI site of the above plasmid and resulting plasmid was designated YEp521-M4.

YEp521-M5 was constructed from YEp521-M4 to add the 50-bp antisense DNA for cdc28 (XhoI fragment) into the msd region. The XhoI site was added into the msd region of YEp521-M4 by PCR. This construct was then digested by XhoI; then the antisense DNA was ligated to the msd region of retron Ec67. This plasmid was transformed into yeast (SP-1) and the subsequently expressed msDNA designated herein as msDNA-Ye117.

Detection of msDNA. A total RNA fraction from yeast cells was prepared as described by Elder et al., *Proc. Natl. Acad. Sci. USA*, 80, 2432–2436, 1983 and a total RNA fraction from *E. coli* was prepared from *E. coli* harboring pC1EP5c by the method described by Chomzynski et al., *Anal. Biochem.*, 162, 156–159, 1987.

To label msDNA with reverse transcriptase, the total RNA fraction prepared from 0.9 ml of a late-log culture was added to 20 μl of a reaction mixture containing 30 mM Tris-HCl (pH 8.2), 50 mM KCl, 10 mM $MgCl_2$, 5 mM DTT, 0.2 mM each of dTTp, dGTP, dCTP, 5 μCi of [-$^{32}$P]dATP and 5 units of avian myeloblastosis virus reverse transcriptase (AMV-RT; Molecular Genetic Resources). The reaction mixture was incubated at 30° C. for 1 hour, and an aliquot of the reaction mixture was subjected to electrophoresis with a 6% polyacrylamide -8M urea gel. Another aliquot was treated with RNase A (10 μg/ml) for 10 minutes at 37° C. and subjected to electrophoresis.

msDNA-Ec67 was also detected by Southern blot analysis (Southern, *Mol. Biol.*, 98, 503–517, 1975). Total RNA from 2.5 ml of a late-log culture was applied to a 1.5% agarose gel with E buffer [40 mM Tris HCl (pH 8.0), 10 mM sodium acetate, 2 mM EDTA ]. After electrophoresis, the gel was blotted to a nylon membrane filter (PALL BLODYNE A TRANSFER MEMBRANE; ICN) by the capillary transfer method. Hybridization was carried out in 50% (v/v) formamide, 5×SSPE; [1×SSPE; 180 mM NaCl, 10 mM sodium phosphate (pH 7.4), 1 mM EDTA], 0.3% sodium dodecyl sulfate, and 5×Denhardt's solution (Denhardt, *Bio-*

*chem. Biophys. Res. Commun.*, 23, 641–646 (1966)) with the nick-translated 140-bp msr-msd region as a probe (Rigby et al., *J. Mol. Biol.*, 113, 237–251, 1977).

As noted above, the invention provides for the expression of the desired msDNAs from eucaryotes in general. While the invention has been illustrated with a yeast of the genus Saccharomyces, others are readily suitable to practice the invention.

A convenient source of suitable yeasts is found in the *ATCC Catalogue of Yeasts*, 18th Ed., 1990. Because of practical and economic importance, the invention is particularly directed to the genus Saccharomyces which is extensively used in baking, beer, wine and other industries. Conventionally these yeasts are referred to as baker's, brewer's and wine yeasts.

Amongst these, of special interest are the *S. cerevisiae* strains, the *S. bayanus, S. carlsbergenensis, S. diataticus,* and *S. uvarum*, which lend themselves to transformation with the vectors of the invention. Further, to express the msDNAs, one may use vertebrate host cells like COS-1, CHO and HeLa cells or invertebrate cells or plant cells.

Plants that may be used include monocotyledons and dicotyledons. Illustrative examples of plants which may be transformed are the following: alfalfa, soybeans, maize and wheat. *Genetic Engineering of Plants, An Agricultural Perspective,* Edited by Kosuge et al., Plenum Press (1983).

To carry out the present invention, various cloning vectors may be used to transfect compatible eucaryotic host cells for replication of the vector. Thereafter the transformants are identified, plasmid DNA prepared therefrom, and the msDNAs extracted and purified.

Vectors for expression of cloned genes in yeasts are described in *Methods in Enzymology,* Vol. 194, "Guide to Yeast Genetics and Molecular Biology", page 373 (Guthrie and Fink, Eds., Academic Press Inc., 1991). It will be apparent from one skilled in the art to select an appropriate promoter for expressing msDNAs in yeast with or without a foreign DNA fragment, such as from regulatable promoters of the GAL family, e.g., GAL4, GAL80, GAL1, GAL2, GAL7, GAL10, GAL11, MEL1; ADH1 and PGK; also see Broach et al., *Experimental Manipulation of Gene Expression,* Academic Press, Inc., New York, 1983 or non-regulatable strong promoters.

Oligonucleotide synthesis may be carried out by a number of methods including those disclosed in U.S. Pat. No. 4,415,734, and in Matteuci et al., *J. Am. Chem. Soc.,* 103 (11):3185–3191 (1981), Adams et al., *J. Am. Chem. Soc.,* 105 (3):661–663 (1983), and Bemcage et al., *Tetrahedron Letters,* 22 (20):1859–1867 (1981).

For the expression of msDNAs in higher eucaryotes with or without selected DNA fragment, one skilled in the art may refer to and use known techniques. The advantages of synthesizing particular eucaryotic proteins in eucaryotes are well known. Depending on the msDNA which is intended to be produced, an appropriate eucaryote host cell will be selected. See *Molecular Cloning: A Laboratory Manual,* Second Edition, §3, §16.3 and seq. (Sambrook et al., Cold Spring Harbor Laboratory Press, 1989). The eucaryotic expression vehicle will contain, as is known, a promoter and enhancer elements, recognition sequences, the TATA box and upstream promoter elements. Other conventional elements located upstream of the transcription initiation site for replication and selection are known and described in standard laboratory manuals. Vectors are available commercially, for instance from Pharmacia (pMSG, pSVT17, pMT2). For methods for introducing recombinant vectors into mammalian cells, see *Molecular Cloning: A Laboratory Manual,* Second Edition, §16.30–16.55, (Sambrook et al., Cold Spring Harbor Laboratory Press, 1989). For cosmid vectors for transfection of mammalian cells, see *Molecular Cloning: A Laboratory Manual, Second Edition,* §23.18 and seq., (Sambrook et al., Cold Spring Harbor Laboratory Press, 1989).

Further, one skilled in the art may wish to refer to *Current Protocols In Molecular Biology,* Volume 1, §16.12–16.13.7 (Ausubel et al., Eds., Greene Publishing Associates and Wiley-Interscience, 1989), discussing in particular, three vector systems or strategies for introducing foreign genes into mammalian cells with COS cells, CHC and vaccinia vital vectors. One skilled in the art will select the most appropriate system for the production of msDNAs from the selected retrons. Further, for introduction of DNA into mammalian cells. See *Current Protocols In Molecular Biology,* Volume 1, §9.01–9.93 (Ausubel et al., Eds., Greene Publishing Associates and Wiley-Interscience, 1989).

The msDNAs have several interesting utilities.

A fascinating utility that is being considered is the role that msDNAs of the invention can play on the formation of triple helix DNA, or triplex DNA with a specific duplex on the chromosome. A recent report in *Science,* 252, 1374–1375 (Jun. 27, 1991), "Triplex DNA Finally Comes of Age", highlights the timeliness of the present invention. Triplex DNA can be formed by binding a third strand to specific recognized sites on chromosomal DNA. Synthetic strands of sizes preferably containing the full complement of bases (such as 11–15 and higher), are discussed. The msDNAs of the invention with long 3' (or 5') ends (and the loop of nonduplexed bases) would appear to be excellent candidates. These regions provide single-stranded DNA necessary for the triplex formation. The resulting triplex DNA is expected to have increased stability and usefulness. New therapies based on the triple helix formation, including in AIDS therapy and selective gene inhibition and others are proposed in the Report.

Artificial, synthetic msDNAs can be designed may be used as antisense DNAs, and/or RNAs and/or ribozymes using the single-stranded DNA or RNA region of msDNAs. Such msDNA (containing a foreign ssDNA or ssRNA fragment) for use as antisense system, has been described above. The production of an msDNA with complementarity with a gene (or portion) thereof, blocks the synthesis of the specific protein itself. The msDNA system produced in eucaryotic cells to generate a desired complementary DNA of an mRNA of a gene, appears to have real potential in eucaryotic cells to block the expression of various harmful or toxic genes, such as drug resistance, oncogenes, and phages or viruses. The system could have applications to AIDS therapy. Of special interest, are the msDNAs that would be produced by HeLa cells and containing such selected DNA fragment for use in antisense applications.

As described above, it is contemplated that genes be inserted for instance, in the the stem region(s) of the msDNAs. Thus the msDNAs may be used for amplification of the selected gene.

The polymerase chain reaction (PCR) is a well-known rapid procedure for in vitro enzymatic amplification of a specific segment of DNA. The standard PCR method requires a segment of double-stranded DNA to be amplified, and always two-single stranded oligonucleotide primers flanking the segment, a DNA polymerase, appropriate deoxyribonucleoside triphosphate (dNTPs), a buffer, and salts (*Current Protocols,* Section 15).

Thus, the msDNAs due to their unique structure (and stability), are expected to be of value in numerous applications in the biochemical, medical, pharmaceutical and other biological sciences.

It can be seen that the present invention is providing a significant contribution to arts and science.

The invention has been described for one skilled in this and selected art. It is intended that the doctrine of equivalents apply to all features and aspects of the invention.

TABLE I

| | Summary of the Structure of msDNA | | | | | | | | |
|---|---|---|---|---|---|---|---|---|---|
| | Structure of msDNA[a] | | | | | | Reverse transcriptase | | |
| | Length of msDNA (nt) | Length of msdDNA (nt) | 3' end overlap length (nt) | Inverted[b] repeat length (nt) | Position of the branched G | Copy number per cell[c] | RT ORF | Distance between msd and RT ORF | Refs. |
| Mx162 | 162 | 77 | 8 | 34 | G-20 | 500–700 | 485 | 77 | * |
| Mx65 | 65 | 49 (62)[d] | 6 | 15 | G-4 (G-17)[e] | 100 | 427 | 28 | ** |
| Sta163 | 163 | 76 | 8 | 33 | G-19 | 500 | ND | ND | *** |
| Ec67 | 67 | 58 | 7 | 13 | G-15 | 500 | 586 | 51 | **** |
| Ec86 | 86 | 82 | 11 | 12 | G-14 | 500 | 320 | 19 | ***** |
| Ec73 | 73 | 75 | 5 | 13 | G-15 | ND | 316 | 53 | ****** |
| Ec107 | 107 | 75[f] | 6 | 16 | G-18 | ND | 319 | 50 | ******* |

[a] See FIG. 1.
[b] The length of the a1 and a2.
[c] Copy numbers are estimated approximately.
[d] On the basis of the inverted repeat structures, the primary product is considered to have a longer 5' arm of 13 bases.
[e] The distance between msd and the first orf. The RT gene overlaps by 4 codons (Sun et al., Science, submitted (1991)).
[f] On the basis of the inverted repeat structures, the lengths of the 5' arm were estimated to be 16, 14, and 17 bases for Mx65, Ec73 and Ec107, respectively.
* Dhundale et al., Cell, 51, 1105–12 (1987) and Yee et al., Cell, 38, 203–9 (1984).
** Dhundale et al., J. Biol. Chem., 263, 9055–58 (1988).
*** Furuichi et al., Cell, 48, 47–53 (1987) and Furuichi et al., Cell, 48, 55–62 (1987).
**** Lampson et al., Science, 243, 1033–38 (1989).
***** Lim and Maas, Cell, 56, 891–904 (1989).
****** Sun et al., Science, submitted (1991).
******* Herzer et al., Mol. Microbiol., submitted (August 1991).

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:1:

TCGATGTAAT TTGCTAATTC ACCGCTCATG TTCGAAGGAT AGTTCTATTT GATC    54

( 2 ) INFORMATION FOR SEQ ID NO:2:

( i ) SEQUENCE CHARACTERISTICS:
        ( A ) LENGTH: 54 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:2:

TCGAGATCAA ATAGAACTAT CCTTCGAACA TGAGCGGTGA ATTAGCAAAT TACA    54

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCAAGCTTCA TAAACACGCA TGT                                                          23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CTGGATCCAG AAACGCATGC AGG                                                          23

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTGGATCCAA GAAATGACAA AAACA                                                        25

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CTGGATCCTT CATTAGCTAT TTAACAT                                                      27

( 2 ) INFORMATION FOR SEQ ID NO:7:

( i ) SEQUENCE CHARACTERISTICS:
        ( A ) LENGTH: 162 base pairs
        ( B ) TYPE: nucleic acid
        ( C ) STRANDEDNESS: single
        ( D ) TOPOLOGY: linear ( i x ) FEATURE:
        ( A ) NAME/KEY: miscfeature
        ( B ) LOCATION: 1
        ( D ) OTHER INFORMATION: /note="The 5'position of this
            nucleotide is linked to the 2'position of
            nucleotide number 20 of SEQ ID NO: 8 of this
            application."

( i x ) FEATURE:
        ( A ) NAME/KEY: miscbinding
        ( B ) LOCATION: 155..162
        ( D ) OTHER INFORMATION: /note="This region can hydrogen
            bond to nucleotides 70-77 of SEQ ID NO: 8 of this
            application."

( x i ) SEQUENCE DESCRIPTION: SEQ ID NO:7:

CATCTTACCT GGGGCACGGT AGCCTCACCG GCTCTCCCCT CCTAGGCACT ACGGCCGGGG                   60

TGGGTAAACG GCGGTCGCGT CGTTGGCTCC GCTACCCACC CTGGCCGTAG TGCCTAGGAG                  120

GGAGAGAGCC AAGAACAGGC TACCTTGCGG AGAGTGTCCT GC                                    162

( 2 ) INFORMATION FOR SEQ ID NO:8:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear (ix) FEATURE:
    (A) NAME/KEY: miscfeature
    (B) LOCATION: 20
    (D) OTHER INFORMATION: /note="The 2'position of this
         nucleotide is linked to the 5'position of
         nucleotide number 1 of SEQ ID NO: 7 of this
         application."

(ix) FEATURE:
    (A) NAME/KEY: miscbinding
    (B) LOCATION: 70..77
    (D) OTHER INFORMATION: /note="This region can hydrogen
         bond to nucleotides 155-162 of SEQ ID NO: 7 of
         this application."

(xi) SEQUENCE DESCRIPTION: SEQ ID NO:8:

```
AGAGGUCCGG AGUGCAUCAG CCUGAGCGCC UCGAGCGGCG GAGCGGCGUU GCGCCGCUCC      60
GGUUGGAAUG CAGGACA                                                     77
```

(2) INFORMATION FOR SEQ ID NO:9:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ix) FEATURE:
        (A) NAME/KEY: miscfeature
        (B) LOCATION: 1
        (D) OTHER INFORMATION: /note="The 5'position of this
             nucleotide is linked to the 2'position of
             nucleotide number 4 of SEQ ID NO: 10 of this
             application."

(ix) FEATURE:
        (A) NAME/KEY: miscbinding
        (B) LOCATION: 60..65
        (D) OTHER INFORMATION: /note="This region can hydrogen
             bond to nucleotides 44-49 of SEQ ID NO: 10 of this
             application."

(xi) SEQUENCE DESCRIPTION: SEQ ID NO:9:

```
CTGCGAGGCG TTGGACCCGG GGCTCCCTGC GTTGCGTACG CTGGGACCCT GGCGAAGAGA      60
TGGGG                                                                  65
```

(2) INFORMATION FOR SEQ ID NO:10:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:
        (A) NAME/KEY: miscfeature
        (B) LOCATION: 4
        (D) OTHER INFORMATION: /note="The 2'position of this
             nucleotide is linked to the 5'position of
             nucleotide number 1 of SEQ ID NO: 9 of this
             application."

(ix) FEATURE:
        (A) NAME/KEY: miscbinding
        (B) LOCATION: 44..49
        (D) OTHER INFORMATION: /note="This region can hydrogen
             bond to nucleotides 60-65 of SEQ ID NO: 9 of this
             application."

(xi) SEQUENCE DESCRIPTION: SEQ ID NO:10:

```
UGAGCCAUGA GUACCGCGGU GUUUCGCCGC GGGGGUGUUC UGUCCCAU                   49
```

(2) INFORMATION FOR SEQ ID NO:11:

( i ) SEQUENCE CHARACTERISTICS:
     ( A ) LENGTH: 163 base pairs
     ( B ) TYPE: nucleic acid
     ( C ) STRANDEDNESS: single
     ( D ) TOPOLOGY: linear ( i x ) FEATURE:
     ( A ) NAME/KEY: miscfeature
     ( B ) LOCATION: 1
     ( D ) OTHER INFORMATION: /note="The 5'position of this
         nucleotide is linked to the 2'position of
         nucleotide number 19 of SEQ ID NO: 12 of this
         application."

( i x ) FEATURE:
     ( A ) NAME/KEY: miscbinding
     ( B ) LOCATION: 156..163
     ( D ) OTHER INFORMATION: /note="This region can hydrogen
         bond to nucleotides 69-76 of SEQ ID NO: 12 of this
         application."

( x i ) SEQUENCE DESCRIPTION: SEQ ID NO:11:

```
CTTCTCACCT  GGGGCACGGT  AGCCTCACCG  GCTCTCCCCT  CCGGTGAGTA  CCTCTCCGGC    60

CGGGGAAACG  GCGGTTGCGT  CGTTGGTTCA  GCTCCCCGGC  CGGAGAGGTA  CTCACCGGAG   120

GGAAGAGAGC  CAAGAACAGG  CTACCTTGCG  GAGAGTGTCC  TGC                     163
```

( 2 ) INFORMATION FOR SEQ ID NO:12:

( i ) SEQUENCE CHARACTERISTICS:
         ( A ) LENGTH: 76 base pairs
         ( B ) TYPE: nucleic acid
         ( C ) STRANDEDNESS: single
         ( D ) TOPOLOGY: linear ( i x ) FEATURE:
         ( A ) NAME/KEY: miscfeature
         ( B ) LOCATION: 19
         ( D ) OTHER INFORMATION: /note="The 2'position of this
             nucleotide is linked to the 5'position of
             nucleotide number 1 of SEQ ID NO: 11 of this
             application."

( i x ) FEATURE:
         ( A ) NAME/KEY: miscbinding
         ( B ) LOCATION: 69..76
         ( D ) OTHER INFORMATION: /note="This region can hydrogen
             bond to nucleotides 156-163 of SEQ ID NO: 11 of
             this application."

( x i ) SEQUENCE DESCRIPTION: SEQ ID NO:12:

```
AGAGGUCCCA  AGCCAUCAGC  CUCAGCGCCU  CGAGCGCGAG  AGCGGCGUUG  CGCCGCUCUG    60

GUUGAAUUGC  AGGACA                                                       76
```

( 2 ) INFORMATION FOR SEQ ID NO:13:

( i ) SEQUENCE CHARACTERISTICS:
         ( A ) LENGTH: 67 base pairs
         ( B ) TYPE: nucleic acid
         ( C ) STRANDEDNESS: single
         ( D ) TOPOLOGY: linear ( i x ) FEATURE:
         ( A ) NAME/KEY: miscfeature
         ( B ) LOCATION: 1
         ( D ) OTHER INFORMATION: /note="The 5'position of this
             nucleotide is linked to the 2'position of
             nucleotide number 15 of SEQ ID NO: 14 of this
             application."

( i x ) FEATURE:
         ( A ) NAME/KEY: miscbinding
         ( B ) LOCATION: 61..67
         ( D ) OTHER INFORMATION: /note="This region can hydrogen
             bond to nucleotides 52-58 of SEQ ID NO: 14 of this (x i) SEQUENCE DESCRIPTION: SEQ ID NO:13:

TCCTTCGCAC AGCACACCTG CCGTATAGCT CTGAATCAAG GATTTTAGGG AGGCGATTCC    60

TCCTGCC    67

(2) INFORMATION FOR SEQ ID NO:14:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (i x) FEATURE:
        (A) NAME/KEY: miscfeature
        (B) LOCATION: 15
        (D) OTHER INFORMATION: /note="The 2'position of this
            nucleotide is linked to the 5'position of
            nucleotide number 1 of SEQ ID NO: 13 of this
            application."

(i x) FEATURE:
        (A) NAME/KEY: miscbinding
        (B) LOCATION: 52..58
        (D) OTHER INFORMATION: /note="This region can hydrogen
            bond to nucleotides 61-67 of SEQ ID NO: 13 of this
            application."

(x i) SEQUENCE DESCRIPTION: SEQ ID NO:14:

CACGCAUGUA GGCAGAUUUG UUGGUUGUGA AUCGCAACCA GUGGCCUUAA UGGCAGGA    58

(2) INFORMATION FOR SEQ ID NO:15:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (i x) FEATURE:
        (A) NAME/KEY: miscfeature
        (B) LOCATION: 1
        (D) OTHER INFORMATION: /note="The 5'position of this
            nucleotide is linked to the 2'position of
            nucleotide number 14 of SEQ ID NO: 16 of this
            application."

(i x) FEATURE:
        (A) NAME/KEY: miscbinding
        (B) LOCATION: 76..86
        (D) OTHER INFORMATION: /note="This region can hydrogen
            bond to nucleotides 72-82 of SEQ ID NO: 16 of this
            application."

(x i) SEQUENCE DESCRIPTION: SEQ ID NO:15:

GTCAGAAAAA ACGGGTTTCC TGGTTGGCTC GGAGAGCATC AGGCGATGCT CTCCGTTCCA    60

ACAAGGAAAA CAGACAGTAA CTCAGA    86

(2) INFORMATION FOR SEQ ID NO:16:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (i x) FEATURE:
        (A) NAME/KEY: miscfeature
        (B) LOCATION: 14
        (D) OTHER INFORMATION: /note="The 2'position of this
            nucleotide is linked to the 5'position of
            nucleotide number 1 of SEQ ID NO: 15 of this
            application."

( i x ) FEATURE:
    ( A ) NAME/KEY: miscbinding
    ( B ) LOCATION: 72..82
    ( D ) OTHER INFORMATION: /note="This region can hydrogen bond to nucleotides 76-86 of SEQ ID NO: 15 of this application."

( x i ) SEQUENCE DESCRIPTION: SEQ ID NO:16:

```
AUGCGCACCC UUAGCGAGAG GUUUAUCAUU AAGGUCAACC UCUGGAUGUU GUUUCGGCAU        60

CCUGCAUUGA AUCUGAGUUA CU                                                 82
```

( 2 ) INFORMATION FOR SEQ ID NO:17:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i x ) FEATURE:
        ( A ) NAME/KEY: miscfeature
        ( B ) LOCATION: 1
        ( D ) OTHER INFORMATION: /note="The 5'position of this nucleotide is linked to the 2'position of nucleotide number 15 of SEQ ID NO: 18 of this application."

( i x ) FEATURE:
        ( A ) NAME/KEY: miscbinding
        ( B ) LOCATION: 69..73
        ( D ) OTHER INFORMATION: /note="This region can hydrogen bond to nucleotides 71-75 of SEQ ID NO: 18 of this application."

( x i ) SEQUENCE DESCRIPTION: SEQ ID NO:17:

```
TTGAGCACGT CGATCAGTTC GCTGATCGGT GGCCCCAGC CGCCGCTCAG CGAACTGAAC         60

GACGGGCATA GCT                                                           73
```

( 2 ) INFORMATION FOR SEQ ID NO:18:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i x ) FEATURE:
        ( A ) NAME/KEY: miscfeature
        ( B ) LOCATION: 15
        ( D ) OTHER INFORMATION: /note="The 2'position of this nucleotide is linked to the 5'position of nucleotide number 1 of SEQ ID NO: 17 of this application."

( i x ) FEATURE:
        ( A ) NAME/KEY: miscbinding
        ( B ) LOCATION: 71..75
        ( D ) OTHER INFORMATION: /note="This region can hydrogen bond to nucleotides 69-73 of SEQ ID NO: 17 of this application."

( x i ) SEQUENCE DESCRIPTION: SEQ ID NO:18:

```
CAGAGCCAAA CCUAGCAUUU UAUGGGUUAA UAGCCCAUCG CGCAUGAGUC AUGGUUUCGC        60

CUAGUAUUUU AGCUA                                                         75
```

( 2 ) INFORMATION FOR SEQ ID NO:19:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear (ix) FEATURE:
    (A) NAME/KEY: miscfeature
    (B) LOCATION: 1
    (D) OTHER INFORMATION: /note="The 5'position of this
        nucleotide is linked to the 2'position of
        nucleotide number 18 of SEQ ID NO: 20 of this
        application."

(ix) FEATURE:
    (A) NAME/KEY: miscbinding
    (B) LOCATION: 102..107
    (D) OTHER INFORMATION: /note="This region can hydrogen
        bond to nucleotides 70-75 of SEQ ID NO: 20 of this
        application."

(xi) SEQUENCE DESCRIPTION: SEQ ID NO:19:

```
CATTAAACCA TCCCGAAGGC GCGTAACTGT ACTGAGCGCG TCAGCGCGAC GTACGCGAAG      60

CGTACTCAGG TACAAATGAG CGAGTTTGGG TATATGGACA TACTACT                  107
```

(2) INFORMATION FOR SEQ ID NO:20:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ix) FEATURE:
        (A) NAME/KEY: miscfeature
        (B) LOCATION: 18
        (D) OTHER INFORMATION: /note="The 2'position of this
            nucleotide is linked to the 5'position of
            nucleotide number 1 of SEQ ID NO: 19 of this
            application."

(ix) FEATURE:
        (A) NAME/KEY: miscbinding
        (B) LOCATION: 70..75
        (D) OTHER INFORMATION: /note="This region can hydrogen
            bond to nucleotides 102-107 of SEQ ID NO: 19 of
            this application."

(xi) SEQUENCE DESCRIPTION: SEQ ID NO:20:

```
CGCCAGCAGU GGCAAUAGCG UUUCCGGCCU UUUGUGCCGG GAGGGUCGGC GAGUCGCUGA      60

CUUAACGCCA GUAGU                                                      75
```

REFERENCES

1. *TIBS*, 16, 18–21 (1991a)
2. *Ann. Rev. Microbiol.*, 45, 163–186 (1991b)
3. Lampson et al., *Progress in Nucleic Acid Research and Molecular Biology*, 60, 1–24
4. *Retroelements*
5. Weiner et al., *Ann. Rev. Biochem.*, 55, 631–661 (1986)
6. Broach et al., *Experimental Manipulation of Gene Expression*, Academic Press Inc., New York, 1983
7. Lampson et al., *Science*, 243, 1033–1038 (1989)
8. Sanger et al., *Proc. Natl. Acad. Sci. USA*, 74, 5463–5467 (1977)
9. Dhundale et al., *Cell*, 51, 1105–1112, 1987
10. Dhundale et al., *J. Biol. Chem.*, 263, 9055–9058, 1988b
11. Furuichi et al., *Cell*, 48, 47–52, 1987a and Furuichi et al., *Cell*, 48, 55–62, 1987b
12. Lima and Maas, *Cell*, 56, 891–904, 1989
13. Sun et al., *J. Bacteriol.*, 173, 4171–4181, 1991
14. Herzer et al., *Mol. Microbiol.*, submitted, August 1991
15. Yanisch-Perron et al., *Gene*, 33, 103–119, 1985
16. Ito et al., *J. Bacteriol.*, 153, 163–168, 1983
17. Kozak, J. *Cell Biology*, 108, 229–241, 1989
18. Boeke et al., *Cell*, 40, 491–500, 1985
19. Hamilton et al., *Nucl. Acids Res.*, 15, 3581–3583, 1987
20. Yee et al., *Cell*, 38, 203–209, 1984
21. Coleman et al., *Cell*, 37, 429–436 (1984)
22. Watson et al., *Molecular Biology of the Gene*, Fourth Ed. (1987), Chapter 18
23. Rose et al., *Methods in Yeast Genetics: A Laboratory Course Manual*, Cold Spring Harbor Lab., Cold Spring Harbor, N.Y., 1990
24. Hoffman and Winston, *Gene*, 57, 268–272, 1987
25. Elder et al., *Proc. Natl. Acad. Sci. USA*, 80, 2432–2436, 1983
26. Chomzynski et al., *Anal. Biochem.*, 162, 156–159, 1987
27. Southern, *Mol. Biol.*, 98, 503–517, 1975
28. Denhardt, *Biochem. Biophys. Res. Commun.*, 23, 641–646 (1966)
29. Rigby et al., *J. Mol. Biol.*, 113, 237–251, 1977
30. *ATCC Catalogue of Yeasts*, 18th Ed., 1990

31. *Genetic Engineering of Plants, An Agricultural Perspective*, Edited by Kosuge et al., Plenum Press (1983)
32. *Methods in Enzymology*, Vol. 194, "Guide to Yeast Genetics and Molecular Biology", page 373 (Guthrie and Fink, Eds., Academic Press Inc., 1991)
33. U.S. Pat. No. 4,415,734
34. Matteuci et al., *J. Am. Chem. Soc.*, 103 (11):3185–3191 (1981)
35. Adams et al., *J. Am. Chem. Soc.*, 105 (3):661–663 (1983)
36. Bemcage et al., *Tetrahedron Letters*, 22 (20):1859–1867 (1981)
37. *Molecular Cloning: A Laboratory Manual*, Second Edition, §3, §16.3 and seq. (Sambrook et al., Cold Spring Harbor Laboratory Press, 1989)
38. *Current Protocols In Molecular Biology*, Volume 1, §16.12–16.13.7 (Ausubel at al., Eds., Greene Publishing Associates and Wiley-Interscience, 1989)
39. *Current Protocols In Molecular Biology*, Volume 1, §9.01–9.93 (Ausubel et al., Eds., Greene Publishing Associates and Wiley-Interscience, 1989)
40. *Science*, 252, 1374–1375 (Jun. 27, 1991), "Triplex DNA Finally Comes of Age"
41. *Current Protocols*, Section 15
42. *Science*, 252, 1643–1650 (Jun. 21, 1991)

We claim:

1. A method for expressing an msDNA in a yeast host cell which comprises transfecting the cell with a DNA expression vector which replicates in the cell, which vector contains a retron encoding the msDNA, which retron contains msr and msd coding regions (msr-msd) for the msDNA and a gene encoding a reverse transcriptase and expressing the msDNA from the retron.

2. The method of claim 1 wherein the expression vector is a plasmid.

3. The method of claim 1 wherein the reverse transcriptase gene is downstream of the msr-msd region.

4. The method of claim 3, wherein the expression vector contains a promoter located upstream of msr, wherein a non-coding DNA fragment of the 5' end upstream of msr, which fragment starts from the promoter and ends immediately upstream of msr, and which contains several AUG codons, has been deleted.

5. The method of claim 1 wherein the reverse transcriptase gene is upstream of the msr-msd region.

6. The method of claim 5 wherein a foreign DNA fragment is contained in the msd region.

7. The method of claim 1 wherein the expression vector contains a promoter located upstream of the msr.

8. The method of claim 7 wherein the promoter is a foreign strong promoter.

9. The method of claim 1 wherein the retron is in vector YEp521-M1.

10. The method of claim 1 wherein the retron is in vector YEp521-M3.

11. The method of claim 1 wherein the retron is in vector YEp521-M4.

12. The method of claim 1 wherein the retron is in vector YEp521-M5.

13. A method for expressing an msDNA in a saccharomyces host cell which comprises transfecting the cell with a DNA expression vector which replicates in the cell, which vector contains a retron encoding the msDNA, which retron contains msr and msd coding regions (msr-msd) for the msDNA and a gene encoding a reverse transcriptase and expressing the msDNA from the retron.

14. The method of claim 13 wherein the msd region contains a cloning site.

15. The method of claim 13 wherein the msDNA molecule comprises a branched single-stranded RNA which is covalently linked to a single-stranded DNA by a 2',5'-phosphodiester bond between the 2'-OH group of an internal rG residue and the 5'-phosphate of the DNA molecule, which RNA is non-covalently linked to the DNA by base-pairing between the complementary 3' ends of the RNA and DNA molecules, which RNA-DNA form stable stem-loop secondary structures, which msDNA is encoded by a primary RNA transcript, pre-msDNA which contains an open-reading frame (ORF) downstream of the msr locus, the ORF encoding a polypeptide having reverse transcriptase activity.

16. The method of claim 13 wherein the msDNA produced is msDNA-Ec67.

17. The method of claim 13 wherein the msDNA which is expressed is selected from the group consisting of msDNA-Mx162, msDNA-Mx65 msDNA-Ec107, msDNA - Mx86 and Sa163.

18. The method of claim 13 wherein the gene encoding reverse transciptase located upstream of the msr region.

19. The method of claim 18 wherein the msDNA produced is msDNA-Ec67.

20. A mammalian cell transfected with a DNA expression vector for replication, which vector contains a retron for msDNA synthesis, which retron contains msr and msd coding regions (msr-msd) of the msDNA and a gene encoding a reverse transcriptase.

21. A yeast host cell transfected with a DNA expression vector for replication, which vector contains a retron for msDNA synthesis, which retrons contains msr and msd coding regions (msr-msd) of the msDNA and a gene encoding a reverse transcriptase.

22. A saccharomyces host cell transfected with a DNA expression vector for replication, which vector contains a retron for msDNA synthesis, which retron contains msr and msd coding regions (msr-msd) of the msDNA and a gene encoding a reverse transcriptase.

23. The saccharomyces host cell of claim 22 wherein the reverse transcriptase gene is downstream of the msr-msd region.

24. The saccharomyces host cell of claim 22, wherein the expression vector contains a promoter located upstream of msr, wherein a non-coding DNA fragment of the 5' end upstream of msr, which fragment starts from the promoter and ends immediately upstream of msr, where the gene encoding the reverse transcriptase is downstream of the msr region, or which fragment starts from the promoter and ends immediately upstream of the gene encoding the reverse transcriptase, where the gene encoding the reverse transcriptase is upstream of the msr region, and which contains several AUG codons, has been deleted but for the initiation codon AUG of the reverse transcriptase gene closest to the 5' end.

25. The saccharomyces host cell of claim 24 wherein the reverse transcriptase gene is upstream of the msr-msd region.

26. The saccharomyces host cell of claim 25 wherein the msd region contains a foreign DNA fragment.

27. The saccharomyces host cell of claim 26 wherein the DNA fragment is 50-bp long.

28. The saccharomyces host cell of claim 22 wherein the expression vector contains the promoter for the msr-msd region and reverse transcriptase gene, which promoter is located upstream of msr.

29. The saccharomyces host cell of claim 28 wherein the promoter is a foreign strong promoter.

30. A DNA expression vector for replication in a yeast host which comprises a retron which encodes a hybrid single- stranded RNA- DNA (msDNA) structure, which retron contains a gene encoding a reverse transcriptase and one coding region which contains two coding sequences, one msr and the other msd for encoding, respectively, the RNA and DNA portions of the msDNA.

31. A DNA expression vector for replication in a saccharomyces host which comprises a retron which encodes a hybrid singe-stranded RNA-DNA (msDNA) structure, which retron contains a gene encoding a reverse transcriptase and one coding region which contains two coding sequences, one msr and the other msd for encoding, respectively, the RNA and DNA portions of the msDNA.

32. The DNA expression vector of claim 31 wherein the reverse transcriptase gene is downstream of the msr-msd region.

33. The vector of claim 32, wherein the expression vector contains a promoter located upstream of msr, wherein a non-coding fragment of the 5' end upstream of msr, which fragment starts from the promoter and ends immediately upstream of msr, and which contains several AUG codons has been deleted.

34. The vector of claim 32 which is YEp521-M1.

35. The vector of claim 31 wherein the reverse transcriptase gene is upstream of the msr-msd region.

36. The vector of claim 35 which is YEp521-M4.

37. The vector of claim 31 which includes a promoter for the msr-msd region and the reverse transcriptase gene, which promoter is located upstream of msr.

38. The vector of claim 37 wherein the promoter is a foreign strong promoter.

39. The vector of claim 38 wherein the promoter is GAL10.

40. The vector of claim 37 which is YEp521-M3.

41. The vector of claim 31 in which a foreign DNA fragment is contained in the msd region of the retron which encodes the DNA of the msDNA.

42. The vector of claim 41 wherein the fragment is 50-bp long.

43. The vector of claim 41 which is YEp521-M5.

44. The DNA expression vector of claim 31 wherein the msr or the msd contains a foreign DNA fragment.

45. The DNA expression vector of claim 44 wherein the msr contains the foreign DNA fragment.

* * * * *

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 1, line 17, change "in" to --- *in* ---
Column 1, line 18, change "vivo" to --- *vivo* ---
Column 1, line 54, change "in vivo" to --- *in vivo* ---
Column 1, line 58, change "in vivo" to --- *in vivo* ---
Column 1, line 60, change "e.g. ," to --- e.g., ---
Column 2, line 5, change "in" to --- *in* ---
Column 2, line 6, change "vivo" to --- *vivo* ---
Column 2, line 8, change "in vivo" to --- *in vivo* ---
Column 2, line 279, change "msr" to --- *msr* ---
Column 2, line 30, change "msd for the msdDNA" to --- *msd* for the *msd*DNA ---
Column 2, line 39, change "msr" to --- *msr* ---
Column 2, line 40, change "msd" to --- *msd* ---
Column 3, line 19, change "EcoRI" to --- *Eco*RI ---
Column 3, line 33, change "XhoI" to --- *Xho*I ---
Column 3, line 33, change "msd" to --- *msd* ---
Column 3, line 39, change "msr-msd" to --- *msr-msd* ---
Column 3, line 43, change "msdRNA (msr)" to --- *msd*RNA (*msr*) ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 3, line 44, change "(msd)" to --- (*msd*) ---
Column 3, line 45, change "msr" to --- *msr* ---
Column 3, line 48, change "msdRNA" to --- *msd*RNA ---
Column 3, line 68, change "msd" --- *msd* ---
Column 4, line 1, change "(msr)" to --- *msr* ---
Column 4, line 4, change "msr" to --- *msr* ---
Column 4, line 5, change "msd" to --- *msd* ---
Column 4, line 25, change "ColE1" to --- *ColE1* ---
Column 4, line 29, change "Sau3A" to --- *Sau3A* ---
Column 4, line 30, change "SalI" to --- *SalI* ---
Column 4, line 32, change "SalI, SalI-to-BamHI, SalI-to-HindIII" to --- *SalI, SalI-to-BamHI, SalI-to-HindIII* ---
Column 4, line 33, change "SalI-to-BclI" to --- *SalI-to-BclI* ---
Column 4, line 36, change "HindIII or HindIII" to --- *HindIII or HindIII* ---
Column 4, line 37, change "BclI" to --- *BclI* ---
Column 4, line 37, change "EcoRI" to --- *EcoRI* ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

Page 3 of 16

It is certified that error appears in the above-indentified patent and that said Letters Patent is hereby corrected as shown below:

Column 4, line 38, change "HindIII" to --- *Hind*III ---
Column 4, line 38, change "BamHI" to --- *Bam*HI ---
Column 4, line 38, change "SalI" to --- *Sal*I ---
Column 4, line 38, change "PstI" to --- *Pst*I ---
Column 4, line 38, change "BclI" to --- *Bcl*I ---
Column 4, line 41, change "EcoRI" to --- *Eco*RI ---
Column 4, line 42, change "(EcoRI" to --- (*Eco*RI ---
Column 4, line 43, change "HindIII" to --- *Hind*III ---
Column 4, line 44, change "msdRNA" to --- *msd*RNA ---
Column 4, line 54, change "msr" to --- *msr* ---
Column 4, line 55, change "msd" to --- *msd* ---
Column 4, line 55, change "msdRNA" to --- *msd*RNA ---
Column 4, line 58, change "GAL10" to --- *GAL*10 ---
Column 4, line 60, change "HindIII" to --- *Hind*III--

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 4, line 60, change "BaII" to --- BaII ---
Column 4, line 60, change "PvuII" to --- PvuII ---
Column 4, line 60, change "BamHI" to --- BamHI ---
Column 4, line 61, change "SmaI" to --- SmaI ---
Column 5, line 11, change "MspI" to --- MspI ---
Column 5, line 26, change "msr-msd" to --- msr-msd ---
Column 5, line 37, change "msd" to --- msd ---
Column 5, line 37, change "XhoI" to --- XhoI ---
Column 5, line 40, change "XhoI" to --- XhoI ---
Column 5, line 41, change "msd" to --- msd ---
Column 5, line 42, change "XhoI" to --- XhoI ---
Column 5, line 43, change "msd" to --- msd ---
Column 6, line 24, change "msr" to --- msr ---
Column 6, line 29, change "msr" to --- msr ---
Column 6, line 36, change "msdRNA" to --- msdRNA ---
Column 6, line 42, change "msr-msd" to --- msr-msd ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 6, line 44, change "msd" to --- msd ---
Column 6, line 44, change "msdRNA" to --- msdRNA ---
Column 6, line 45, change "msr" to --- msr ---
Column 6, line 48, change "msd" to --- msd ---
Column 6, line 49, change "msr" to --- msr ---
Column 6, line 50, change "msd" to --- msd ---
Column 6, line 51, change "msd" to --- msd ---
Column 6, line 52, change "msr" to --- msr ---
Column 6, line 57, change "msd-msr" to --- msd-msr ---
Column 6, line 63, change "msd-msr" to --- msd-msr ---
Column 6, line 65, change "msd" to --- msd ---
Column 6, line 66, change "msr" to --- msr ---
Column 6, line 68, change "msd" to --- msd ---
Column 7, line 6, change "msd" to --- msd ---
Column 7, line 8, change "msr" to --- msr ---
Column 7, line 24, change "msr-msd" to --- msr-msd ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 7, line 28, change "msr-msd" to --- msr-msd ---
Column 7, line 29, change "msr" to --- msr ---
Column 7, line 33, change "msr-msd" to --- msr-msd ---
Column 7, line 34, change "msr-msd" to --- msr-msd ---
Column 7, line 57, change "msr-msd" to --- msr-msd ---
Column 7, line 59, change "msr-msd" to --- msr-msd ---
Column 7, line 65, change "(pre-msdRNA" to --- pre-msdRNA
    ---
Column 7, line 66, change "msr" to --- msr ---
Column 8, line 1, change "msdRNA" to --- msdRNA ---
Column 8, line 6, change "msr-msd" to --- msr-msd ---
Column 8, line 25, change "ColE1" to --- ColE1 ---
Column 8, line 31, change "BalI-PvuII" to --- BalI-PvuII
    ---
Column 8, line 32, change "BalI" to --- BalI ---
Column 8, line 32, change "PvuII" to --- PvuII ---
Column 8, line 34, change "HincII" to --- HincII ---
Column 8, line 39, change "PstI(a)-EcoRI" to --- PstI(a)-
    EcoRI ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 8, line 40, change "BalI-PvuII" to --- *BalI-PvuII* ---

Column 8, line 44, change "EcoRI" --- *EcoRI* ---
Column 8, line 46, change "HindIII" to --- *HindIII* ---
Column 8, line 48, change "BclI" to --- *BclI* ---
Column 8, line 49, change "HindIII" to --- *HindIII* ---
Column 8, line 51, change "EcoRI" to --- *EcoRI* ---
Column 8, line 53, change "HindIII-BamHI" to --- *HindIII-BamHI* ---
Column 8, line 54, change "HindIII" to --- *HindIII* ---
Column 8, line 54, change "BamHI" to --- *BamHI* ---
Column 8, line 56, change "msr-msd" to --- *msr-msd* ---
Column 8, line 63, change "msr-msd" to --- *msr-msd* ---
Column 9, line 15, change "msr-msd" to --- *msr-msd* ---
Column 9, line 44, change "HindIII" to --- *HindIII* ---
Column 9, line 47, change "msr" to --- *msr* ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 9, line 48, change "HindIII" to --- HindIII ---
Column 9, line 48, change "msr" to --- msr ---
Column 9, line 50, change "msr-msd" to --- msr-msd ---
Column 9, line 51, change "msd" to --- msd ---
Column 9, line 52, change "msr-msd" to --- msr-msd ---
Column 9, line 53, change "msd) two" to --- msd) ---
Column 9, line 57, change "HindIII" to --- HindIII ---
Column 9, line 57, change "BamHI" to --- BamHI ---
Column 9, line 63, change "msr-msd" to --- msr-msd ---
Column 9, line 64, change "msr-msd" to --- msr-msd ---
Column 9, line 66, change "msr-msd" to --- msr-msd ---
Column 10, line 1, change "msr-msd" to --- msr-msd ---
Column 10, line 4, change "msr-msd region was reversed,
     i.e., the msr-msd region" to --- msr-msd region was
     reversed, i.e., the msr-msd region ---
Column 10, line 7, change "BamHI" to --- BamHI ---
Column 10, line 16, change "msd" to --- msd ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 10, line 7, change " Hind III " to -- Hind III --.

Column 14, line 47, change " lac " to -- lac --.

Column 10, line 18, change "msr-msd" to --- *msr-msd* ---
Column 10, line 54, change "msd" to --- *msd* ---
Column 11, line 6, change "msr-msd" to --- *msr-msd* ---
Column 11, line 15, change "msr-msd" to --- *msr-msd* ---
Column 11, line 25, change "msr-msd" to --- *msr-msd* ---
Column 11, line 27, change "msr-msd" to --- *msr-msd* ---
Column 11, line 57, change "Sal1" to --- *Sal1* ---
Column 11, line 63, change "pyrE and ttk" to --- *pyrE* and *ttk* ---
Column 12, line 2, change "msd" to --- *msd* ---
Column 12, line 3, change "msr" to --- *msr* ---
Column 12, line 5, change "SalI(b)-EcoRI(c)" to --- *SalI(b)-EcoRI(c)* ---
Column 12, line 8, change "PstI" to --- *PstI* ---
Column 12, line 36, change "msd" to --- *msd* ---
Column 12, line 37, change "msd" to --- *msd* ---
Column 12, line 40, change "msdRNA" to --- *msdRNA* ---
Column 12, line 48, change "msr-msd" to --- *msr-msd* ---
Column 12, line 49, change "msr-msd" to --- *msr-msd* ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 12, line 60, change "in vivo" to --- in vivo ---
Column 12, line 65, change "in vivo" to --- in vivo ---
Column 13, line 14, change "msd" to --- msd ---
Column 13, line 17, change "XhoI" to --- XhoI ---
Column 13, line 19, change "XhoI" to --- XhoI ---
Column 13, line 23, change "msr" to --- msr ---
Column 14, line 26, change "XhoI" to --- XhoI ---
Column 14, line 33, change "msd" to --- msd ---
Column 14, line 33, change "msr" to --- msr ---
Column 14, line 44, change "msd" to --- msd ---
Column 14, line 48, change "msd" to --- msd ---
Column 15, line 12, change "endA1 recA1 hsdR17 (rk, k+)
     supE44" to --- endA1 recA1 hsdR17 (rk, k+) supE44
     ---
Column 15, line 13, change "thi-1, gyrA96, relA1)" to ---
     thi-1, gyrA96, relA1 ---
Column 15, line 22, change "ColE1" to --- ColE1 ---
Column 15, line 25, change "BalI-PvuII" to --- BalI-PvuII
     ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 15, line 29, change "HincII" to --- *Hinc*II ---
Column 15, line 32, change "PstI(a)-EcoRI" to --- *Pst*I(a)-*Eco*RI ---
Column 15, line 33, change "Bal-I-PvuII" to --- *Bal*-I-*Pvu*II ---
Column 15, line 45, change "EcoRI" to --- *Eco*RI ---
Column 15, line 47, change "HindIII" to --- *Hind*III ---
Column 15, line 50 change "HindIII" to --- *Hind*III ---
Column 15, line 52 change "EcoRI" to --- *Eco*RI ---
Column 15, line 53, change "HindIII-BamHI" to --- *Hind*III-*Bam*HI ---
Column 15, line 54, change "HindIII" to --- *Hind*III ---
Column 15, line 54, change "BamHI" to --- *Bam*HI ---
Column 15, line 55, change "msr-msd" to --- *msr-msd* ---
Column 15, line 60, change "msr" to --- *msr* ---
Column 15, line 68, change "msr-msd" to --- *msr-msd* ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 16, line 2, change "HindIII" to --- HindIII ---
Column 16, line 2, change "BamHI" to --- BamHI ---
Column 16, line 3, change "HindIII" to --- HindIII ---
Column 16, line 3, change "BamHI" to --- BamHI ---
Column 16, line 5, change "msr-msd" to --- msr-msd ---
Column 16, line 6, change "BamHI" to --- BamHI ---
Column 16, line 7, change "BamHI" to --- BamHI ---
Column 16, line 16, change "BamHI" to --- BamHI ---
Column 16, line 17, change "BamHI" to --- BamHI ---
Column 16, line 20, change "the msr-msd region and the RT
gene. The msr-msd" to --- the msr-msd region and the RT
gene. The msr-msd ---
Column 16, line 23, change "SmaI" to --- SmaI ---
Column 16, line 23, change "BamHI" to --- BamHI ---
Column 16, line 24, change "BamHI" to --- BamHI ---
Column 16, line 25, change "SmaI" to --- SmaI ---
Column 16, line 25, change "msr" to --- msr ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 16, line 26, change "msd" --- *msd* ---
Column 16, line 26, change "SmaI" to --- *Sma*I ---
Column 16, line 30, change "(XhoI" to --- (*Xho*I ---
Column 16, line 31, change "msd" to --- *msd* ---
Column 16, line 31, change "XhoI" to --- *Xho*I ---
Column 16, line 32, change "msd" to --- *msd* ---
Column 16, line 33, change "XhoI" to --- *Xho*I ---
Column 16, line 34, change "msd" to --- *msd* ---
Column 17, line 2, change "msr-msd" to --- *msr-msd* ---
Column 17, line 7, change "Saccharomyces" to --- *Saccharomyces* ---
Column 17, line 12, change "Saccharomyces" to --- *Saccharomyces* ---
Column 17, line 41, change "GAL" to --- *GAL* ---

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

```
Column 17, line 43, change "PGK" to --- PGK ---
Column 33, line 31, change "msr and msd coding regions
     (msr-msd)" to --- msr and msd coding regions (msr-
     msd) ---
Column 33, line 37, change "msr-msd" to --- msr-msd ---
Column 33, line 39, change "msr" to --- msr ---
Column 33, line 41, change "msr" to --- msr ---
Column 33, line 42, change "msr" to --- msr ---
Column 33, line 45, change "msr-msd" to --- msr-msd ---
Column 33, line 47, change "msd" to --- msd ---
Column 33, line 49, change "msr" to --- msr ---
Column 33, line 65, change "msr and msd" to --- msr and
     msd ---
Column 33, line 66, change "(msr-msd)" to --- (msr-msd)
     ---
Column 34, line 1, change "msd" to --- msd ---
Column 34, line 24, change "msr" to --- msr ---
Column 34, line 30, change "msr" to --- msr ---
```

UNITED STATES PATENT AND TRADEMARK OFFICE
CERTIFICATE OF CORRECTION

PATENT NO. : 5,436,141
DATED : July 25, 1995
INVENTOR(S) : Miyata et al.

It is certified that error appears in the above-indentified patent and that said Letters Patent is hereby corrected as shown below:

Column 34, line 31, change "msd coding regions (msr-msd)" to --- *msd* coding regions (*msr-msd*) ---

Column 34, line 36, change "msr and msd coding regions (msr-msd)" to --- *msr* and *msd* coding regions (*msr-msd*) ---

Column 34, line 41, change "msr and msd coding regions (msr-msd)" to --- *msr* and *msd* coding regions (*msr-msd*) ---

Column 34, line 45, change "msr-msd" to --- *msr-msd* ---

Column 34, line 48, change "msr" to --- *msr* ---

Column 34, line 49, change "msr" to --- *msr* ---

Column 34, line 50, change "msr" to --- *msr* ---

Column 34, line 52, change "msr" to --- *msr* ---

Column 34, line 57, change "msr" to --- *msr* ---

Column 34, line 61, change "msr-" to --- *msr-* ---

Column 34, line 62, change "msd" to --- *msd* ---

Column 34, line 64, change "msd" to --- *msd* ---

Column 35, line 1, change "msr-msd" to --- *msr-msd* ---

Column 35, line 2, change "msr" to --- *msr* ---

UNITED STATES PATENT AND TRADEMARK OFFICE
CERTIFICATE OF CORRECTION

PATENT NO.  : 5,436,141
DATED       : July 25, 1995
INVENTOR(S) : Miyata et al.

It is certified that error appears in the above-indentified patent and that said Letters Patent is hereby corrected as shown below:

```
Column 36, line 2, change "msr" to --- msr ---
Column 36, line 6, change "msr-msd" to --- msr-msd ---
Column 36, line 9, change "msr-msd" to --- msr-msd ---
Column 36, line 10, change "msr" to --- msr ---
Column 36, line 17, change "msd" to --- msd ---
Column 36, line 23, change "msr or the msd" to ---msr or
    the msd ---
Column 36, line 25, change "msr" to --- msr ---
```

Signed and Sealed this

Twenty-fifth Day of November, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,436,141
DATED         : July 25, 1995
INVENTOR(S)   : Miyata et al.

It is certified that error appears in the above-identified patent and that said Letters Patent is hereby corrected as shown below:

Column 1,
Line 15, before "FIELD OF THE INVENTION", please insert the following paragraph:

-- The U.S. Government has a paid-up license in this invention and the right in limited cricumstances to require the patent owner to license others on reasonable terms as provided for by the terms of Grant Nos. GM26843 and GM44012 awarded by the NIH. --

Signed and Sealed this

Fifteenth Day of July, 2003

JAMES E. ROGAN
*Director of the United States Patent and Trademark Office*